United States Patent [19]

Janmey et al.

[11] Patent Number: 5,691,160
[45] Date of Patent: Nov. 25, 1997

[54] EFFECTS OF ACTIN FILAMENTS OF FIBRIN CLOT STRUCTURE AND LYSIS

[75] Inventors: Paul A. Janmey, Arlington, Mass.; Jennifer A. Lamb, Chicago, Ill.; Stuart E. Lind; Thomas P. Stossel, both of Belmont, Mass.

[73] Assignee: Biogen, Inc., Cambridge, Mass.

[21] Appl. No.: 929,203

[22] Filed: Aug. 14, 1992

[51] Int. Cl.$^6$ .............................. C12Q 1/56; C12Q 1/06; G01N 33/86

[52] U.S. Cl. .............................. 435/13; 435/39; 435/213; 435/240.1; 436/16; 436/63; 436/69; 530/324; 530/350; 530/351; 530/382; 530/412; 514/2; 514/21

[58] Field of Search .............................. 435/13, 39, 213, 435/240.1; 436/16, 63, 69; 530/350, 381, 324, 382, 412; 514/2, 21

[56] References Cited

U.S. PATENT DOCUMENTS

| | | | |
|---|---|---|---|
| 5,177,001 | 1/1993 | Yamamoto | 435/68.1 |
| 5,177,002 | 1/1993 | Yamamoto | 435/68.1 |
| 5,260,224 | 11/1993 | Stossel et al. | 436/503 |
| 5,326,749 | 7/1994 | Yamamoto | 514/8 |
| 5,464,817 | 11/1995 | Stossel | 514/2 |
| 5,508,265 | 4/1996 | Stossel | 514/12 |

FOREIGN PATENT DOCUMENTS 297946  6/1988  European Pat. Off.

OTHER PUBLICATIONS

D. J. Kwiatkowski et al., "Plasma and Cytoplasmic Gelsolins Are Encoded By A sSingle Gene and Contain A Duplicated Actin–Binding Molecule," *Nature*, 323, pp. 455–458 (1986).
D. J. Kwiatkowski et al., "Identification of Critical Functional and Regulatory Domains in Gelsolin," *J. Cell Biol.* 108, pp. 1717–1726 (1989).
Journey et al, *Blood*, vol. 80, No. 4, pp. 928–936, Aug. 15, 1992.
Lind et al, *J. Clin. Invest.*, vol. 78, pp. 736–742, Sep. 1986.
Haddad et al, *Proc. Natl. Acad. Sci. USA*, vol. 87, pp. 1381–1385, Feb. 1990.
Smith et al, *J. Lab. Clin. Med.*, vol. 110, No. 2, pp. 189–195, Aug. 1987.
Andre, E. et al., *The Journal of Biological Chemistry* 263(2):722–727 (1988).
Carr, M.E. et al., *J. Lab. Clin. Med.* 96(6):985–993 (1980).
Carr, M.E., *Thrombosis and Haemostasis* 59(3):535–539 (1988).
Carr, M.E. et al., *J. Lab. Clin. Med.* 110(6):747–752 (1987).
Carrell, N. et al., *Blood* 62(2):439–447 (1983).
Dhall, T.Z. et al., *Thrombosis and Haemostasis* 35:737–745 (1976).
Dhall, T.Z. et al., *Thrombosis and Haemostasis* 49(1):42–46 (1983).
Gabriel, D.A. et al., *J. Lab. Clin. Med.* 101(4):545–552 (1983).
Goldschmidt–Clermont, P.J. et al., *Gastroenterology* 94:1454–1458 (1988).
Goldschmidt–Clermont, P.J. et al., *J. Clin. Invest.* 81:1519–1527 (1988).
Haddad, J.G. et al., *Proc. Natl. Acad. Sci. USA* 87:1381–1385 (1990).
Harper, K.D. et al., *Clinical Research* 36(3):625A (1988).
Harper, K.D. et al., *J. Clin. Invest.* 79:1365–1370 (1987).
Janmey, P.A. et al., *Blood* 70(2):524–530 (1987).
Janmey, P.A. et al., *Biochimica et Biophysica Acta* 841:151–158 (1985).
Kamykowski, G.W. et al., *Biophysical Chemistry* 13:25–28 (1981).
Laki, K. et al., *Biochimica et Biophysica Acta* 371:519–525 (1974).
Lee, W.M. et al., *Circulatory Shock* 28:249–255 (1989).
Lee, W.M. et al., *Hepatology* 7(5):825–830 (1987).
Lind, S.E. et al., *Am. Rev. Respir. Dis.* 138:429–434 (1988).
Lind, S.E. et al., *J. Clin. Invest.* 78:736–742 (1986).
Pollard, T.D. et al., *Ann. Rev. Biochem.* 55:987–1035 (1986).
Procyk, R. et al., *Biopolymers* 29:559–565 (1990).
Smith, D.B. et al., *American Journal of Pathology* 130(2):261–267 (1988).
Smith, D.B. et al., *Blood* 72(1):214–218 (1988).
Smith, D.B. et al., *J. Lab. Clin. Med.* 110:189–195 (1987).
Stossel, T.P. et al., *Ann. Rev. Cell Biol.* 1:353–402 (1985).
Suenson, E. et al., *Biochimica et Biophysica Acta* 870:510–519 (1986).
International Search Report for International Application No. PCT/US93/07584, mailed Oct. 14, 1993.
Janmey, P.A. et al., Effects of actin filaments on fibrin clot structure and lysis, *Biological Abstracts* 94(10):AB–953, Abstract No. 111777 (1992).
Kawamura, K. et al., Quantivitative determination of vitamin–D–binding protein in body fluids, *Chemical Abstracts* 104, Abstract No. 145140w (1986).
Lind, S.E. et al., Actin Is a Noncompetitive Plasmin Inhibitor, *J. Biol. Chem.* 266(8):5273–5278 (1991).
Lind, S.E. et al., Human Plasma Gelsolin Binds to Fibronectin, *J. Biol. Chem.* 259(21):13262–13266 (1984).
Ohsawa, M., Binding of actin to serum actin–binding proteins and determination of actin in blood of cadavers using anti Gc, *Chemical Abstracts* 111, Abstract No. 2243r (1989).

*Primary Examiner*—Cecilia J. Tsang
*Assistant Examiner*—Abdel A. Mohamed
*Attorney, Agent, or Firm*—Leslie M. Levine

[57] ABSTRACT

The present invention relates to therapeutic methods wherein an actin-binding protein, preferably gelsolin or DBP, is administered to a patient with actin-containing clots in order to remove actin from the clots. The invention also relates to diagnostic methods in which actin is removed from an actin-containing clot in vitro and quantitated.

16 Claims, 13 Drawing Sheets

EFFECTS OF ACTIN FILAMENTS OF FIBRIN CLOT STRUCTURE AND LYSIS

This invention was made with government support; the government has certain rights in the invention.

FIELD OF THE INVENTION

The invention generally relates to therapeutic and diagnostic methods for treating patients with tissue injury in which free extracellular actin is associated with blood clots. The present invention relates to a method to assay the amount of actin present in a fibrin clot. The method involves the in vitro quantitation of the amount of actin in the clot by incubation of the clot in vitro with proteins that bind actin. The invention is specifically related to incubation of such clots in the presence of the plasma actin binding proteins gelsolin and vitamin D-binding protein. The invention is also directed to methods of removing actin from blood clots in vivo by administering actin-binding proteins to subjects with blood clots.

BACKGROUND OF THE INVENTION

Tissue injury results in the activation of the coagulation cascade, leading to deposition of fibrin. During inflammatory events, molecules not normally found in plasma may enter the extracellular space, potentially affecting blood coagulation. Some of these molecules may arise from the action of cellular proteases upon normal plasma constituents (e.g., fibrinogen), the release of granules of inflammatory cells, or disruption of cellular plasma membranes. Extensive studies of the effects of fibrinogen degradation products upon fibrin clot formation (Shen et al., *J. Biol. Chem.* 252:6184 (1977)) have provided important information about the mechanisms whereby inflammatory events lead to alterations in the process of blood coagulation. Molecules that alter the fibrin gel formation and clot structure (Dhall et al., *Thromb. Haemost.* 35:737 (1976); Carr and Gabriel, *J. Lab. Clin. Med.* 96:985 (1980); Gabriel et al., *J. Lab. Clin. Med.* 101:545 (983); Chow. et al., *Thromb. Res.* 29:243 (1983); Cart et al., *J. Lab. Clin. Med.* 110:747 (1987); Karnykowski et al., *Biophys. Chem.* 13:25 (1981); Procyk and King, *Biopolymers* 29:559 (1990)) may play a role in determining the hemostatic effectiveness of fibrin clots, as well as their ability to mediate fibrin-dependent fibrinolysis (Suenson and Petersen, *Biochim. Biophys. Acta* 870:510 (1986); Dhall et al., *Thrombos Haemostas* 49:42 (1983)).

Injury to animal tissues results in the release of actin into the extracellular space, including the bloodstream. Actin is the most abundant protein in animal cells and constitutes 10-20% of the protein of many nucleated cells and 30% of the protein of muscle cells. Actin molecules each bind an ATP molecule and self-assemble into long filaments during which the ATP is hydrolyzed into ADP. Although approximately half of nonmuscle cell actin is F-actin, (the double-helical, rodlike, filament form of actin which is assembled from G-actin monomers), the ionic conditions of extracellular fluids favor actin polymerization, so that virtually all the actin released into the blood from dying cells would be expected to polymerize into filaments (Lind et al., *Am. Rev. Respir. Dis.* 138:429434 (1988)). In purified solutions, in the absence of filament-shortening proteins, actin filaments can easily attain lengths of several microns. Were some fraction of actin released from injured cells to be irreversibly denatured, however, or else bound to one of the intercellular actin-binding proteins discussed below, this actin would remain monomeric.

Actin, has been found at micromolar concentrations in plasma or serum of animals and humans experiencing a variety of types of tissue injury (Smith et al., *J. Lab. Clin. Med.* 110:189 (1987); Smith et al., *Am. J. Pathol.* 130:261 (1988); Smith et al., *Blood* 72:214 (1988); Goldschmidt-Clermont et at., *Gastroenterology* 94:1454 (1988); Lee et al., *Hepatology* 7:825 (1987); Lee et al., *Circ. Shock* 28:249 (1989); Lind et al., *Am. Rev. Resp. Dis.* 138:429 (1988)). In vitro this globular protein assembles into rodlike filaments many microns in length, and in vivo, it exchanges rapidly between monomeric and polymeric forms, a process regulated in the cytoplasm by a number of actin-binding proteins (Stossel et at., *Ann. Rev. Cell Biol.* 1:353 (1985)). When added to fibrinogen solutions, actin filaments may interfere with the process of fibrin clot formation, by sterically hindering the diffusion of fibrin protofibrils into bundles (Janmey et al, *Biochim. Biophys. Acta* 841:151 (1985)).

Because of the large amounts of actin in cells, the release of actin from dying cells provides sufficient actin to have a significant effect on the microenvironment, by increasing the viscosity of extracellular fluids of plasma, by entrapping cells, by other, as yet unidentified toxic effects, and, as discussed below, by changing the physicochemical properties of fibrin clots. Infusion of extracellular free actin is toxic to animal tissues, and especially to renal and cardiopulmonary systems (Harper et al., *Clin. Res.* 36:625A (1988); Haddad et al., *Proc. Natl. Acad. Sci. U.S.A.* 87:1381-1385 (1990)). Acute renal failure is a complication of muscle injury and actin infusions in rats causes transient elevations of the BUN and creatinine levels, consistent with renal failure.

Moreover, since each extracellular actin molecule in a filament has an ADP molecule associated with it, the presence of extracellular actin in the blood may tend to induce or augment platelet aggregation in a manner which may not be advantageous to the host (Lind et al., *Am. Rev. Respir. Dis* 138:429–434 (1988); Scarborough et al., *Biochem. Biophy. Res. Commun.* 100:1314–1319 (1981)).

There are many proteins which naturally associate with actin (for a review of actin-binding proteins see Stossel et al., *Ann. Rev. Cell Biol.* 1:353–402 (1985); Pollard et al., *Ann. Rev. Biochem.* 55:987–1035 (1986)). However, two proteins, gelsolin (also called "brevin" and "actin depolymerizing factor") and vitamin D binding protein (also called Gc globulin) (DBP) are thought to be primarily responsible for binding extracellular actin (Janmey et al., *Blood* 70:529–530 (1987)).

Mammalian blood plasma contains micromolar concentrations of these two proteins that bind to actin with high affinity. (Janmey and Lind, *Blood* 70:524 (1987)). High affinity actin-binding proteins bind actin with a $K_d$ of less than $10^{-8}$. Both gelsolin and DBP bind to actin in serum and have actin depolymerizing activity. DBP preferentially binds monomeric actin while gelsolin preferentially binds actin filaments.

Gelsolin is a multifunctional actin-binding protein obtained from mammalian cytoplasm and extracellular fluids. Plasma gelsolin differs from cellular gelsolin only by the addition of 25 amino acids at the amino terminus of the molecule and both gelsolins are the product of a single gene. Plasma gelsolin has three actin-binding sites and binds with high affinity to either G-actin or F-actin.

Plasma gelsolin binds a second actin molecule with a higher affinity than it binds a first actin molecule, and thus preferentially forms 2:1 complexes over 1:1 complexes and binds filaments in preference to monomers. When added to F-actin, plasma gelsolin severs the filament in a nonproteolytic manner and remains bound to one end of the newly formed filament. If free gelsolin molecules are present, they will sever the actin filament successively until only 2:1 actin-gelsolin complexes are present, thereby rapidly depolymerizing the filament.

Free and complexed (to actin) gelsolin molecules differ in their functional properties. Although free gelsolin can sever actin filaments, actin-gelsolin complexes cannot.

Gelsolin's primary function in the plasma is to sever actin filaments. If gelsolin is present in excess of actin, only gelsolin-actin complexes result; if actin is in vast excess, there are free actin oligomers and gelsolin-actin complexes. The actin severing occurs by way of a nonproteolytic cleavage of the noncovalent bond between adjacent actin molecules (subunits). Gelsolin's severing activity is activated by micromolar $Ca^{++}$ and has been shown to be inhibited by phosphatidylinositol bisphosphate (PIP2) and phosphatidyl inositol monophosphate (PIP). Since extracellular $Ca^{2++}$ concentrations are at millimolar levels and extracellular fluids do not normally contain PIP or $PIP_2$ in a form that inhibits gelsolin, plasma gelsolin is constitutively active in extracellular fluids.

Vitamin D-binding protein (DBP), on the other hand, has a single actin binding site and binds only to monomeric actin (Van Baelin et al., *J. Biol. Chem.* 255:2270 (1980); Haddad, J. G., *Arch. Biochem. Biophys.* 213:538 (1982)). Both plasma gelsolin and DBP serve to clear actin from the circulation (Lind et al., *J. Clin. Invest.* 78:736 (1986); Harper et al., *J. Clin. Invest.* 79:1365 (1987); Goldschmidt-Clermont et al. , *J. Clin. Invest.* 81:1519 (1988)). DBP has recently been shown to prevent microvascular thrombosis brought about by the injection of monomeric actin into experimental animals (Haddad et at., *Proc. Natl. Acad. Sci. U.S.A.* 87:1381 (1990)). Plasma gelsolin and DBP thus constitute a defense system designed to protect the host against deleterious effects of actin released into the circulation.

It has been proposed that the binding of extracellular actin to gelsolin or DBP protects against F-actin formation in the circulation and may be the mechanism by which such actin is targeted for removal from the bloodstream (Lind et al., *J. Clin. Invest.* 78:736–742 (1986); Sanger et al., *Clin. Res.* 36:625A (1988)). For example, it is known that circulating actin-gelsolin complexes are found following oleic-acid induced lung injury in rabbits and cats (Smith et al., *Am. J. Path.* 130:261–267 (1988)) and in phenylhydrazine-induced hemolysis in rabbits (Smith et al., *Blood* 72:214–218, 1988) ). In the clinical setting, gelsolin levels are depressed in patients with the adult respiratory distress syndrome (ARDS) (Lind et al., *Am. Rev. Respir. Dis.* 138:429–434 (1988)), and in the plasma of patients with acute falciparum malaria infection (Smith et al., *Blood* 72:214–218 (1988)), and gelsolin actin complexes are detectable in the blood of such patients. In addition, complexes of actin with DBP have been observed in the plasma of patients with fulminant hepatic necrosis (Young et al., *J. Lab. Clin. Med.* 110:83 (1987)). It has also been proposed that once the ability of plasma proteins to bind extracellular free actin is exceeded, intravascular filament formation and enclothelial injury can be detected (Harper et al., *Clin. Res.* 36:625A (1988); Haddad et al., *Proc. Natl. Acad. Sci.* 87:1381–1389 (1990)).

Gelsolin has been cloned (Kwiatkowski et al., *Nature* 323:455–458 (1986); Kwiatkowski et al., *J. Cell Biol.* 106:375–384 (1988)) and fragments of the native protein which retain the ability to bind actin have been identified (Bryan, J., *J. Cell Biol.* 106:1553–1562 (1988); Yin et al., *J. Cell Biol.* 107:465a (1988), abst. no. 2616); Kwiatkowski et al., *J. Cell Biol.* 108:1717–1726 (1989); Way et al., *J. Cell Biol.* 109:593–605 (1989)). DBP has also been cloned (Cooke et al., *J. Clin. Invest.* 76:2420–2424 (1985); Yang et al., *Proc. Natl. Acad. Sci. U.S.A.* 82:7994–7998 (1985)).

Hemostasis depends on a balance between formation and dissolution of clots composed of fibrin networks and varying proportions of other plasma proteins and blood cells. These networks form by the polymerization of fibrin monomers into protofibrils, and the subsequent lateral association of protofibrils into bundles, which takes place in vivo in a complex (and potentially variable) mixture of other proteins. Because fibrin clot formation is sensitive to the effects of macromolecules that impede the diffusion of the growing polymer strands, a number of physiologically important molecules, such as IgG, fibronectin, albumin, glycosaminoglycans, etc. (Carr and Gabriel, *J. Lab. Clin. Med.* 96:985 (1980); Gabriel et al., *J. Lab. Clin. Med.* 101:545 (1983); Carr et al., *J. Lab. Clin. Med.* 110:747 (1987); Carr et al., *J. Lab. Clin. Med.* 107:199 (1986); Carr et al., *Thromb. Res.* 45:539 (1987); Carr et al., *Biochemistry* 28:1384 (1989)), alter the structure of fibrin gels. Many of these substances are normal constituents of plasma, and may explain in part the recognized differences between plasma clots and those formed from purified fibrinogen. Studies of these effects on fibrin clots have suggested mechanisms whereby inflammatory events lead to alterations in the process of blood coagulation (Carr, M. E., *Thromb. Haemost.* 59:535 (1988)).

Clots that form at sites of tissue injury are likely to be different from those prepared from normal plasma however, and may contain proteins released from platelets, white cells, enclothelial cells or other types of injured cells, as well as acute phase proteins. While much previous investigation of the bleeding and thrombotic tendencies noted in patients suffering from different forms of tissue injury has focused on the dysregulation of the clotting and fibrinolytic systems, collectively known as disseminated intravascular coagulation, little consideration has been given to the structure and function of the clots that form in such patients, which could be altered in clinically significant ways. Conformational changes in fibrin clots, for example, may render them more susceptible to disruption by mechanical forces, whether found naturally in the vascular tree or imposed by medical devices such as membrane oxygenators or mechanical ventilators. Alternatively, alterations in clot structure may affect their sensitivity to the fibrinolytic protein plasmin, rendering them resistant to plasmin's action, in a manner analogous to that reported for a patient with a congenital dysfibrinogenemia (Carrell et al., *Blood* 62:439 (1983)). The possibility that actin and perhaps other intracellular proteins released during tissue trauma may exert these effects is suggested by the finding that material released from platelets alters both the structure and lysis of fibrin clots in vitro (Dhall et al., *Thrombos Haemostas* 49:42 (1983)).

It is known that actin impairs the normal sequence of blood coagulation and fibrinolytic events. Recent findings concerning the interaction of actin with fibrinolytic proteins indicate that actin might affect fibrin gel structure and function. Actin is able to promote plasmin formation when added to solutions containing Glu-plasminogen and t-PA (Lind and Smith, *J. Biol. Chem.* 266:17673 (1991)). When actin-containing clots are placed in a lysis bath containing plasminogen and t-PA, however, clot lysis is inhibited. While experiments with purified proteins suggest that actin is a non-competitive plasmin inhibitor (Lind and Smith, *J. Biol. Chem.* 266:5273 (1991)), an effect of actin on fibrin clot structure may also account for some of its inhibitory effects upon clot lysis.

Actin has previously been shown to interact with fibrin (Laki and Muszbek, *Biochim. Biophys. Acta* 371:519 (1974)) and may be cross-linked to it in vitro by the action of Factor XIIIa (Mui and Ganguly, *Am. J. Physiol.* 233:H346 (1977)). It has been reported that actin filaments alter fibrin clot structure, resulting in the formation of fine, less turbid, clots. Addition of gelsolin, a protein that shortens actin filaments, abrogates this effect, indicating that actin filaments intertwine with fibrin fibrils, inhibiting their lateral association (Janmey et al., *Biochim. Biophys. Acta* 841:151 (1985)).

The rheology of fibrin clots is thus an important aspect of their physiologic functioning. The present invention is based on the discovery of the effects of actin upon the mechanical properties fibrin clots.

An assay which can be used to assess the quantity of actin in fibrin clots in vivo, particularly where extensive tissue injury has taken place, is of clinical value. Such a method can be used diagnostically to determine therapeutic regimens necessary to counteract the effect of free extracellular actin in injured patients. A treatment regimen which removes actin from an actin-containing clot is also of therapeutic importance with respect to restoring normal viscoelastic properties to clots in vivo.

DESCRIPTION OF THE FIGURES

FIG. 7. Effect of actin filament length on fibrin rheology during clot lysis with plasmin. Increase and decrease of dynamic shear modulus (G') measured in the torsion pendulum, of fibrin alone (open circles) or fibrin with actin (closed circles) as a function of time. The fibrinogen concentration was 3 mg/ml and the F-actin concentration was 0.25 mg/ml.

SUMMARY OF THE INVENTION

Figure 1:
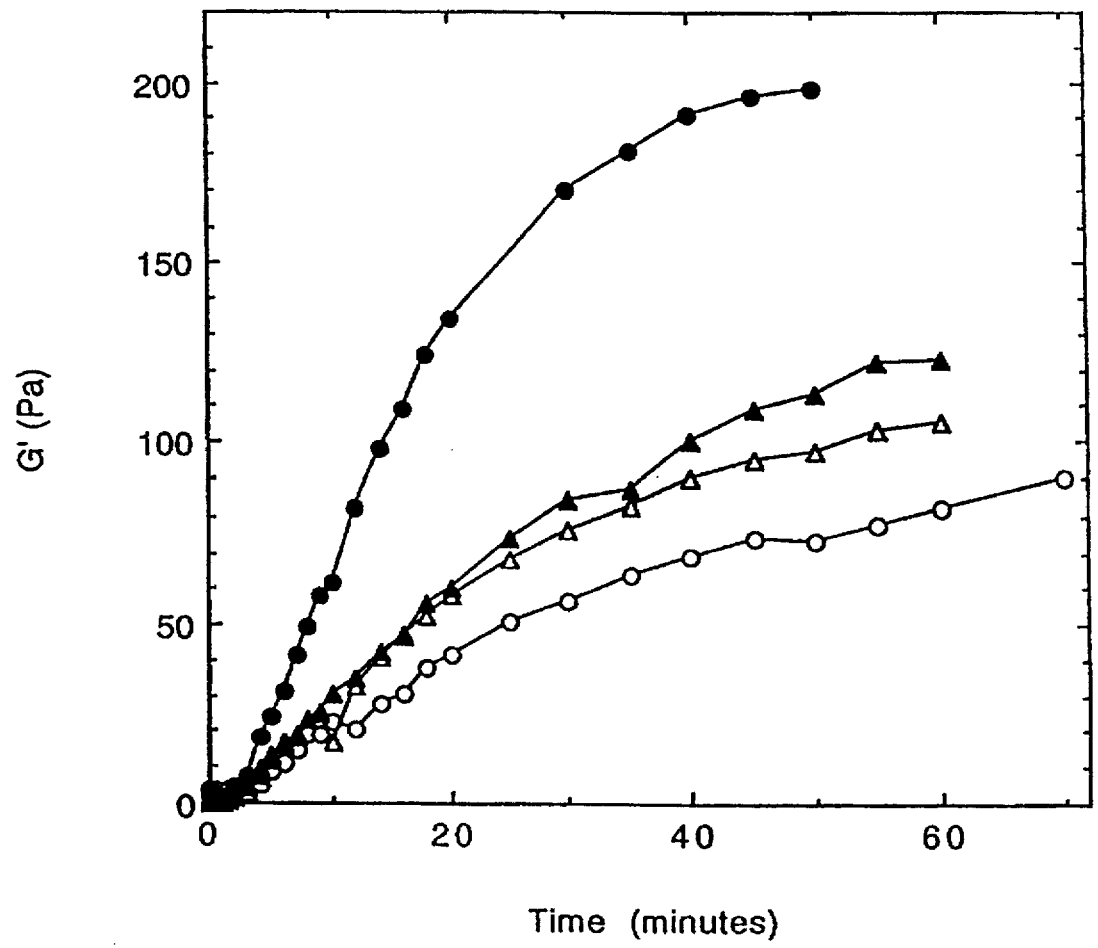
FIG. 1. Effect of F-actin on fibrin rheology. Increase in dynamic storage modulus (G') following addition of thrombin to fibrinogen, measured by oscillatory shear deformations of 2% strain amplitude and angular frequency 10 rad/s (1.6 Hz). The fibrinogen concentration was 2.0 mg/ml, and the actin concentration (in mg/ml) was 0 (open circles); 0.2 (open triangles); 0.4 (closed triangles); and 1.0 (closed circles). All solutions contained 150 mM NaCl, 2.2 mM $CaCl_2$, 150 µM ATP, 1.9 mM $MgCl_2$, pH 7.4. G-actin was added to fibrinogen and 0.1 NIH unit/ml thrombin was added 10 s later.

The present invention is based upon the inventors' consideration that administration of actin-binding compounds, or biologically active derivatives thereof, to subjects, after tissue injury, will provide protection to other healthy tissues by restoring normal viseoelastic properties to actin-containing clots. It is therefore an object of the invention to provide a method for decreasing levels of actin in clots formed in the blood stream and extracellular space of an animal. It is therefore an object of the invention to provide a method for releasing the actin in actin-containing clots formed in vivo. It is a further object of the invention to provide therapeutic treatments which can be used to treat an animal to protect against secondary tissue injury which occurs due to abnormal actin levels such that actin-containing clots with altered viseoelastic properties are formed in vivo.

The present invention is also based upon the inventors' discovery that actin filaments trapped in fibrin clots may be eluted from the clot by incubation in the presence of an actin binding-protein and quantitated. Accordingly, the present invention is also directed to a procedure of potential therapeutic importance wherein plasma is isolated from patients with tissue injury, clots are allowed to form, and the clots are then incubated in the presence of an actin-binding protein, and the actin released therefrom quantitated. This procedure provides an assay to assess the amount of actin trapped in fibrin clots in vivo in the plasma of patients with various types of tissue injury.

It is therefore an object of the invention to provide a method to accurately assess the properties of clots in patients in vivo, wherein said patients have extensive tissue injury by quantitating the amount of actin filaments trapped in those clots.

DESCRIPTION OF THE PREFERRED EMBODIMENTS

In order to provide a clearer and consistent understanding of the specification and claims, including the scope to be given such terms, the following definitions are provided.

Actin-binding compound. "Actin-binding compound" is meant to include any compound, and especially any protein (or peptide), which is capable of binding actin so as to modify any of actin's many functions, including suppressing the ability of actin monomers to polymerize into filaments and which is substantially free of natural contaminants which associate with such compound either in vivo (in a prokaryotic or eukaryotic) host, or in vitro (as a result of a chemical synthesis). Such compounds include, but are not limited to extracellular actin-binding proteins such as gelsolin and DBP, and intracellular actin-binding proteins such as those most abundant in cells (for example, myosins, tropomyosins, proillin and cofilin) and those most abundant in non-muscle cells. Actin-binding compounds within the scope of the methods of the invention also include but are not limited to a) actin-binding compounds that predominantly sequester actin monomers, that is, bind monomers in a complex which is resistant to polymerization (for example, DBP, profilin, depactin, cofilin, and DNAase I); b) actin-binding compounds which sequester monomers and possess filament severing activity (for example, gelsolin, villin, fragmin and severin; c) actin-binding compounds that predominantly block the ends of actin filaments and prevent the exchange of monomers with that end (for example, capping protein, β-actinin, and acumentin); and d) actin-binding nonproteinaceous molecules that have such effects on actin (for example, cytochalasin or biologically-active derivatives thereof, that block the ends of actin filaments).

If desired, such compounds may be administered in the form of a pharmaceutically acceptable salt to the subject.

Thrombotic event. By the term "thrombotic event" is meant any vascular condition in which vascular occlusion, thrombosis, infarction or other biological perturbation results in fibrinolysis.

Actin-containing clot. By the "actin-containing clot," for the purpose of the invention, is intended a clot according to the definition immediately below wherein the clot contains actin filaments and/or actin monomers on the clot fiber or actin filaments trapped in the interstices of the fibrin network. The actin contained in the clot may be the result of trapping, covalent bonding, and other types of bonding such as hydrogen, ionic, and other noncovalent types of physicochemical interaction. Actin may also be contained in the clot as a result merely of trapping.

Clot. By the term "clot," for the purpose of the invention, is intended a soft, nonrigid insoluble mass formed when blood gels. The term clot particularly applies to the coagulated phase of blood; the soft, coherent, jelly-like red mass resulting from the conversion of fibrinogen to fibrin, thereby entrapping the red blood cells (and offer formed elements) within the coagulated plasma. The clot may be formed either in or out of the body. Some clots may appear yellow because of settling out of the erythrocytes before the occurrence of clotting. This type of clotting may occur when clots are allowed to form outside of the body. Blood clots may also be external type clots, which are clots are formed outside of a blood vessel. Internal clots are formed within a blood vessel. Muscle clots may be formed by coagulation of muscle plasm. A blood clot may also be composed of fibrin and platelets. When so formed, the clot is termed a washed or white clot.

Tissue Injury. By the term "tissue injury," for the purpose of the present invention, is a tissue injury that results in thrombosis. Such injuries include but are not limited to pneumonia, trauma, myocardial infarction, or any organ infarction, but in particular, myocardial infarction because the heart contains significant quantifies of actin. Crush injuries are also relevant to the present invention because skeletal muscle contains significant amounts of actin. The type of injury which is relevant to the present invention is that type of injury that releases actin into the extracellular space via blood cells or fixed tissue cells as well as the release of thromboplastic materials which causes fibrin clot formation in such areas so that the fibrin clot traps the actin. In general, the cell injury to which the invention is directed is an injury in which there is inflammation and cell injury as well as clotting formation so that the cell injury could be fragmentation of neutrophils or platelets in the blood or damage to fixed organs like the heart or the liver.

Animal. The term "animal" is meant to include all animals in which the accumulation of free actin or actin filaments in the bloodstream or extracellular space would be detrimental to the physiology of the animal. Foremost among such animals are humans; however, the invention is not intended to be so limiting, it being within the contemplation of the present invention to treat any and all animals which may experience the beneficial effect of the invention.

Efficacious Amount. An "efficacious amount" of an actin-binding compound is one which is sufficient to release actin from an actin-bound clot formed from an animal with tissue injury.

An efficacious amount an actin-binding compound is also one which is sufficient to reduce or eliminate the amount of actin found in an actin-containing clot in vivo.

Substantially Free of Natural Contaminants. A material is said to be "substantially free of natural contaminants if it has been substantially purified from materials with which it is normally and naturally found before such purification. Examples of natural contaminants with which actin-binding compounds might be associated are: non-actin-binding peptides, carbohydrates, glycosylated peptides, lipids, membranes, etc. A material is said to be substantially free of natural contaminants if those contaminants normally and naturally found with the substance in vivo or in vitro are substantially absent from a sample of the material. By "substantially absent" is meant that such contaminants are either completely absent or are present at such low concentrations that their presence (1) does not interfere with the desired effect of the active agent (herein the actin-binding compound) in the preparation when such preparation is incubated with the actin-containing fibrin clot to which the present invention is directed.

By "substantially absent" is also meant that such contaminants are either completely absent or are present at such low concentrations that their presence does not interfere with the desired therapeutic effect of the active agent (herein the actin-binding compound) in the preparation when such preparation is administered to an animal and does not harm the animal as a result of the administration of the preparation.

Administration. The term "administration is meant to include introduction of actin-binding compounds to any animal by any appropriate means known to the medical art, including, but not limited to, enteral and parenteral (e.g., intravenous) administration.

Treatment. The term "treatment" or "treating" is intended to include the administration of actin-binding compounds to a subject for purposes which may include prophylaxes, in amelioration, prevention, or cure of actin-related disorders.

Incubation. The term "incubation" is meant to include introduction of actin-binding compounds.

Pharmaceutically Acceptable Salt. The term "pharmaceutically acceptable salt" is intended to include salts of the actin-binding compounds of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Vehicle. The term "pharmaceutically acceptable vehicle" is intended to include solvents, carders, diluents, and the like, which are utilized as additives to preparations of the actin-binding compounds of the invention so as to provide a carrier or adjuvant for the administration of such compounds.

Fragment. The term "fragment" is meant to include any portion of a molecule which provides a segment of an actin-binding compound which is capable of binding actin monomers; the term is meant to include actin-binding fragments which are made from any source, such as, for example, from naturally-occurring peptide sequences, synthetic or chemically-synthesized peptide sequences, and genetically engineered peptide sequences. Further, if such fragment is a peptide, a fragment of a peptide of such actin-binding protein is meant to include to any variant of the actin-binding protein.

Variant. A "variant" of a compound such an actin-binding compound is meant to refer to a compound substantially similar in structure and biological activity to either the native compound, or to a fragment thereof.

The biological activity of the compounds of the invention is their ability to bind actin and modify it into a form so that it can be released from a fibrin clot in vitro. Such modification may be the result of the binding of the compounds per se or the result of a chemical or enzymatic reaction which results from such binding.

Functional Derivative. A "functional derivative" of an actin binding compound is a derivative which possesses a biological activity that is substantially similar to the biological activity of the actin-binding compound. By "substantially similar" is meant activity which is quantitatively different but qualitatively the same. For example, a functional derivative of an actin-binding protein of the invention would contain the same amino acid backbone as an actin-binding protein but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of an actin binding compound. Such derivatives may improve the compound's solubility, absorption, biological half life, etc. The derivatives may also decrease the toxicity of the molecule, or eliminate or attenuate any undesirable side effect of the molecule, etc. Derivatives and specifically, chemical moieties capable of mediating such effects are disclosed in Remington's Pharmaceutical Sciences (1980). Procedures for coupling such moieties to a molecule are well known in the art. The term "functional derivative" is intended to include the "fragments," "variants," "analogues," or "chemical derivatives" of a molecule.

Analog. An "analog" of the actin-binding compounds of the invention is meant to refer to a compound substantially similar in function to either the native actin-binding compound or to a fragment thereof. For example, an analog of an actin-binding protein is a protein which does not have the same amino acid sequence as an actin-binding protein but which is sufficiently homologous to an actin-binding protein so as to retain the biological activity of such actin-binding protein.

The Applicants have discovered that there are two types of actin-fibrin interactions. A relatively non-specific interaction is due to trapping of actin filaments within the fibrin gel, and a more specific type of binding occurs even when actin filaments are shorter than the average pore size of the fibrin gel. The addition of vitamin D-binding protein, which binds to actin monomers and prevents them from polymerizing into actin filaments, has an effect upon the amount of actin bound to clots that resembles the effect of plasma gelsolin. Both proteins inhibit binding, supporting the idea that fibrin clots trap actin filaments. Depression of the plasma content of either protein in the vicinity of a forming clot would therefore probably result in increased amounts of clot-associated actin. That some actin binds to fibrin even when equimolar concentrations of these actin-binding proteins are present is not surprising, since a specific interaction between actin and fibrin is implied by the cross-linking of actin to fibrin by Factor XIIIa (Mui and Ganguly, Am. J. Physiol. 233:H346 (1977)).

The theological properties of actin-containing clots differ from those of pure fibrin clots, as would be expected when two interdigitating filament networks are mixed together. Previous workers have shown that the rheologic properties of actin and fibrin networks differ both quantitatively and qualitatively, and the viscoelasticity of a mixture of two such polymers is difficult to predict (Janmey et al., J. Cell. Biol. 113:155–160 (1991)); Janmey et al., J. Rheol. 27:135 (1983)). The Applicants have discovered that incorporation of actin into a fibrin clot leads to a disappearance of one of its unusual properties, strain-hardening, and lessens its ability to withstand large deformations without structural change. Clots containing actin are thus more brittle than those without. Addition of gelsolin, which solates the actin network, prevents this effect, suggesting that the brittleness of actin/fibrin clots is due more to steric interactions between the two filament types than to direct actin/fibrin binding. In short, actin can be incorporated into fibrin clots without compromising their physical properties as long as the filaments are not too long.

Gelsolin thus exerts a protective effect upon fibrin clots when added to actin before the fibrin clot is formed. By shortening actin, gelsolin decreases the amount of actin associated with the clot and maintains the clot's rheologic properties. In addition, gelsolin is able to shorten actin filaments trapped in a fibrin clot, allowing much of the clot-associated actin to diffuse from the clot. These experiments also confirm that clot-associated actin inhibits plasmin-mediated fibrinolysis. Removal of actin from a clot by plasma gelsolin can thus be considered to be beneficial insofar as it aids in the restoration of the homeostatic mechanisms that regulate clot formation and dissolution.

Accordingly, the present invention is directed to a method for removing or reducing the actin in a clot in vivo by the administration of efficacious amounts of an actin-binding protein. In a preferred embodiment, gelsolin, DBP, or actin-binding fragments thereof, or a combination of gelsolin and DBP and/or actin-binding fragments thereof are provided to the subject in need of treatment.

In one embodiment, efficacious levels of actin-binding compounds are administered so as to release actin associated with clots in vivo and thus to counteract the effect of excessive extracellular actin on clot formation in vivo. By "efficacious levels of actin-binding compounds" is meant level in which the toxic effects of free extracellular actin are, at a minimum, ameliorated. The toxic effects of free extracellular actin, with respect to the present invention, are those toxic effects that are the result of detrimental alterations in the viscoelastic properties or the rate of lysis of clots in vivo. By "excessive extracellular actin" is meant an mount of extracellular actin which exceeds the ability of the actin-hiding proteins to bind and clear the actin from extracellular fluids without secondary incidental tissue damage or toxic effects. By "secondary tissue damage or toxic effects" is meant the tissue damage or toxic effects which occur to otherwise healthy tissues, organ's, and cells therein, due to the presence of actin-containing clots, usually as a result of a primary tissue injury elsewhere in the body.

In the methods of the invention, infusion of actin-binding compounds, such as gelsolin, DBP, or actin-binding fragments thereof, result in the reduction or complete removal of actin from actin-containing clots in vivo.

Actin-binding compounds may be conjugated either chemically or by genetic engineering, to fragments of other agents which provide a targeting of such actin-binding compounds to a desired site of action. Alternatively, other compounds may be conjugated either chemically or by genetic engineering, to other actin-binding compound or active-fragment thereof, so as to enhance or provide additional properties to such actin-binding compound, especially properties which enhance the compound's ability to promote release of actin's toxic effects. For example, because actin promotes intravascular blood coagulation and inhibits fibrinolysis, by conjugating tissue plasminogen activator and/or an antithrombin such as hirudin or active fragments thereof to the actin-binding compound, one can target a fibrinolytic agent to the sites where tissue injury released actin which promoted the formation of actin-binding clots.

Amounts and regimens for the administration of actin-binding compounds can be determined readily by those with ordinary skill in the clinical art of treating actin-related disorders, tissue injury and inflammation. Generally, the dosage of actin-binding compound treatment will vary depending upon considerations such as: type of actin-binding compound employed; age; health; conditions being treated; kind of concurrent treatment, if any, frequency of treatment and the nature of the effect desired; extent of tissue damage; gender; duration of the symptoms; and, counterindications, if any, and other variables to be adjusted by the individual physician. Dosage can be administered in one or more applications to obtain the desired results.

The dosage can be calculated in the following manner. The normal blood gelsolin concentration is 2.4 μM (2.4 μmol/L) and the normal blood DBP concentration is 5 μM (5 μmol/L). For gelsolin the normal actin-binding capacity is 4.8 μM. Thus, the total blood actin-binding capacity (ABC) is approximately 9.8 μmol/L. The blood volume is 6% of the body weight, hence a 70 Kg person has 4.2 liters of blood and thus (4.2 L×7.5 μmol/L) 31.5 μmols ABC. Since DBP and gelsolin are distributed throughout the extracellular space (which is 10% of the body weight), the body contains (7.5×7) 52.5 μmols ABC.

It may be desired to administer between 32 and 53 μmols of an actin binding compound (or 0.46 μmol/kg body weight) to cover total complexing or depletion of endogenous ABC. Since 42.5 mg of actin is equal to 1 μmol, and since there is 4.86 mg actin per gram of skeletal muscle, each gram of muscle contains 0.114 μmol actin, or 460 grams of muscle destruction could neutralize total body ABC. However, because the toxic effects of actin are presumably local (e.g., inhibition of clot lysis), sequestered or kinetically determined (e.g., actin permeates an organ faster than binding proteins neutralize it), it is likely that a theoretically minimum dose will have to be adjusted upward in order to achieve kinetically favorable therapeutic effects. The kinetic effect can be important, for example, since hemolysis of about half of erythron, which should liberate only 4.2 μmol of actin, reduces the plasma gelsolin concentration by half acutely (Smith et al., *Blood* 72:214–2181 (1988)), suggesting slow equilibration between extravascular and blood compartments. Conversely, a therapeutically effective state, capable of breaking up local deposits of actin, may be achievable only by a transient pulse of a high concentration of actin-binding molecules.

The compounds of the invention can be administered in any appropriate pharmacological carrier for administration. They can be administered in any form that effects prophylactic, palliative, preventative or curing conditions of tissue injury in humans and animals.

Preparations of the actin-binding proteins of the invention for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The actin-binding proteins of the invention may also be administered by means of pumps, or in sustained-release form, especially, when the primary injury is prolonged or delayed rather an acute. An example in which the primary injury is often prolonged or delayed rather than acute is a myocardial infarction wherein the damage to the heart muscle is not revealed (or persists) until days after the primary heart attack. The actin binding molecules of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated. For example, it is desirable to administer the actin-binding proteins of the invention in a sustained-release form when the methods of the invention are being used to treat a genetic or chronic disease based upon an actin-related disorder so as to maximize the comfort of the patient.

The actin-binding proteins of the invention can be employed in dosage forms such as tablets, capsules, powder packets, or liquid solutions for oral administration if the biological activity of the protein is not destroyed by the digestive process and if the characteristics of the compound allow it to be absorbed across the intestinal tissue.

The pharmaceutical compositions of the present invention are manufactured in a manner which is in itself known, for example, by means of conventional mixing, granulating, dragee-making, dissolving, lyophilizing or similar processes. The compositions of the present invention, in and of themselves, find utility in the control of actin-induced physiological damage, be it chronic or acute. The compositions of the invention direct the body's own mechanisms for dealing with excess actin in the bloodstream or extracellular tissues to its maximum potential. In intravenous dosage form, the compositions of the present invention have a sufficiently rapid onset of action to be useful in the acute management of potential tissue damage.

Additionally, a low potency version is useful in the management of mild or chronic actin-related disorders.

In addition, the compositions of the present invention provide requisite reagents for the laboratory assay of actin levels in an animal's bloodstream or extracellular tissues.

Efficacious mounts of an actin binding protein, particularly DBP, gelsolin or any active fragment thereof which are substantially free of natural contaminants can be administered to a patient who has had a severe myocardial infarction or other thrombotic event for a time and period throughout which damage to the heart or tissue is revealed. The amount of the peptide to be administered may be determined after assaying the ratio of total to bound gelsolin in the patient's plasma to determine the fraction of the total gelsolin which has already been saturated with actin released by the dying heart cells and calculating the amount needed to, at a minimum, supply enough actin-binding capability to return this ratio to levels found in healthy individuals. Further, indicators of renal damage such as the patient's BUN and creatinine levels may be closely monitored and the dose of the actin-binding molecule adjusted higher, if necessary, if such indicators reveal that renal damage may be occurring.

Thus, the present invention may be used to administer actin-binding compounds to animals in levels sufficient to either a) prevent actin filament formation and/or b) process actin filaments to a "stable" monomeric state, in amounts sufficient to treat and/or prevent undesirable physiological effects of free actin accumulation or release in the bloodstream.

The particular actin-binding molecules that are the subject of the methods of the invention are purified native and recombinant actin-binding proteins, and other non-proteinaceous actin-binding molecules, and biologically-active fragments thereof, which are characterized by the presence of unique actin binding domains which possess the biological activity of being able to sequester actin in a monomeric form or rapidly to disaggregate or depolymerize actin filaments or to cover sites on free actin that are toxic to host cells. Individual actin-binding domains possessing this biological activity may also be produced by synthetic, enzymatic, proteolytic, chemical or recombinant DNA methods.

The methods of the invention are based also in part upon the unexpected discovery of the Applicants that a fibrin clot containing actin filaments, if incubated in the presence of the actin-binding protein, gelsolin, releases the actin into the incubation medium from which the actin may be quantitated.

In a preferred embodiment, gelsolin, DBP, or actin-binding fragments thereof, or, a combination of gelsolin and DBP and/or actin-binding fragments thereof, are incubated in vitro with the actin-containing clot.

In one embodiment, efficacious levels of actin-binding compounds are administered so as to release actin associated with clots formed in vitro from plasma of subjects with tissue injury. By "efficacious levels" of actin-binding compounds is meant levels in which the clot-associated actin can be released and measured and thus to allow diagnosis of the effects of excessive extracellular actin on clot formation in vivo. By "excessive" extracellular actin is meant an amount of extracellular actin which exceeds the ability of the plasma proteins to bind and clear the actin from extracellular fluids without secondary tissue damage or toxic effects.

In a preferred embodiment of the invention, plasma is withdrawn from a subject with tissue injury and clots are allowed to form in vitro. The preferable conditions for clotting are described in Example V. Clots are then removed from the container in which they were formed and incubated with increasing mounts of an actin-binding protein, preferably gelsolin or DBP. The clot is dissolved in SDS or urea or other known solubilizing agent and then is subjected to gel electrophoresis. Gels may be based on polyacrylamide or any of the other gel media well known to those skilled in the art as effective to separate proteins. Following gel electrophoresis, a Western blot procedure is applied and the actin released from the clot, if any, is detected with anti-actin antibody. In order to assess the amount of gelsolin necessary to release the actin in the clot, various mounts of gelsolin are added to various clots to assess the mount necessary to release the majority or all of the actin from the clot. When the concentration at which the release of actin is complete or reaches a plateau, that amount of gelsolin is established as being effective. Subsequently, the incubation medium from the procedure in which the maximally effective actin-binding protein has added, may be used to quantitate the amount of actin released from the clot by immunoprecipitation of actin-binding protein-actin complexes in the incubation medium. Following maximal release of actin from the clots, the amount of actin may be completely titrated by the addition of exogenous actin-binding protein, for example, gelsolin or DBP. Anti actin-binding antibodies, such as anti-gelsolin or anti-DPB may be used to immunoprecipitate and subsequently quantitate the complexes. Alternatively, anti-actin antibodies may be used to detect the actin released into the incubation medium by immunoprecipitation of actin-anti-actin antibody complex.

In an alternative preferred embodiment, a clot is formed in a small chromatography tube. Through the tube is applied an actin-binding protein solution, preferably gelsolin or DBP or fragments thereof. The eluate is then measured by standard ELISA or the actin-binding protein is immunoprecipitated and the presence of complexes with actin are assayed by gel electrophoresis, preferably polyacrylamide gel electrophoresis. The parameters are described below.

Fibrinogen is prepared at a concentration between 0.1–10.0 milligrams per milliliter, preferably 2–3 mg/ml. The pH is between 6 to 8.5, preferably 7.4. The ionic strength is between 50 and 500 mM, preferably 100 mM. The buffer is an imidazole or tris buffer. The calcium concentration is between 0.1–10 mM, preferably about 0.3 mM. The ATP concentration is 10 µM through 10 mM. Around 0.5 ml of fibrinogen is added to a 1 cm diameter chromatography column and allowed to form an approximately 1 millimeter clot by adding between 0.01–10 NIH units, preferably 0.1 NIH unit per ml of thrombin. The clot thus formed is mechanically strong enough to withstand fluid permeation without collapsing and porous enough to allow the permeation to occur at a rate of about 0.2 milliliters per minute. Clot formation takes about 1 to 10 minutes. After ten times the clotting time, between 1 and 10 cm of pressure is applied to the chromatography tube. The level of the incubating buffer is then adjusted until the flow rate is about 0.2 milliliters per minute. Pressure is adjusted by observing the meniscus of the clot. When the meniscus of the clot starts to collapse, the pressure is slightly relieved. Thus, fluid is allowed to permeate through the clot in the above described buffer. The buffer at first does not contain gelsolin. The buffer is used to wash the clot free of non-specifically held protein. Gelsolin is then added to the buffer and the gelsolin-containing buffer is washed through the clot in about 1 to 5 minutes. The eluted fractions are assayed for actin by applying the fractions to a gel, particularly SDS polyacrylamide, and immunoblotting with anti-actin antibody. The gelsolin concentration is between 50 nM and 5 µM, preferably between 1 and 5 µM.

In an alternative assay, an assay of lysis by plasmin may be used to determine the amount and rate of actin released from clots by an actin-binding protein, preferably gelsolin or DBP. Since actin inhibits plasmin-based lysis, the rate of lysis of a clot may then be used as a measure of actin release. The rate of lysis is increased as actin is removed from an actin-containing clot. In cases in which this type of assay is used, clots are formed in chromatography tubes as described above or taken out of the tube and incubated in buffer with or without the actin-binding protein, preferably gelsolin or DBP.

Alternative methods of detecting actin released from a clot exploits the parameter of strain-hardening. Strain-hardening may be measured by methods described in detail in the exemplary material below. Strain-hardening is diminished in actin-containing clots and may be regained when actin is released from clots. Therefore, the release of actin in clots may be quantitated by the rheological measurements described in the exemplary material.

Actin-binding proteins which are substantially free of natural contaminants can be isolated and purified from their natural or recombinant sources in accordance with conventional conditions and techniques in the art previously used to isolate such proteins, such as extraction, precipitation, chromatography, affinity chromatography, electrophoresis, or the like.

One of skill in the art can identify the actin-binding domain(s) of an actin-binding compound using techniques known in the art, without undue experimentation, and such domains are preferred in the methods of the invention. For example, derivatives of the native actin-binding proteins, or, derivatives of recombinantly produced actin-binding proteins, can be made by proteolytic cleavage of the full-length actin-binding protein with common proteases, such as, for example, trypsin, chymotrypsin, and subtilisin. Affinity chromatography with actin-derivatized resins may be used to assay such fragments for their actin-binding ability.

When identification of compounds or fragments thereof which possess actin-severing activity is desired, such compounds or fragments can also be identified using techniques known in the art, for example, by following the rate of depolymerization of pyrene-labeled F-actin.

Further, such fragments may be identified by their homology to other known actin-binding or actin-severing domains wherein it may be predicted that function will follow homology. For example, it is known that severin, gelsolin and villin, and especially amino acid residues 40–351 in severin and amino acid residues 63–383 in gelsolin, show extensive homology in the domain responsible for F-actin severing activity.

The N-terminal half of gelsolin, for example, an N-terminal tryptic fragment known as CT45, is capable of severing F-actin and contains two actin binding sites. One of these sites resides in a chymotryptic fragment, CT15N (human gelsolin residues 24–150), which binds the ends of actin monomers and filaments with high affinity; the other site is contained in the adjacent fragment CT28N (residues 151–406), which binds to the side of F-actin in a polyphosphoinositide-regulated manner. Neither of the fragments sever actin filaments by themselves. The smallest gelsolin polypeptide which is capable of severing F-actin encompasses residues 25–165 of plasma gelsolin.

Further, compounds such as actin-binding proteins are highly conserved among species and can be easily isolated in large quantities from nonhuman (bovine, porcine) plasma and/or muscle tissues and fragments of these proteins can be chemically or enzymatically prepared by techniques well-known in the art. Thus such actin-binding compounds can be administered to a subject in need of the therapeutic methods of the invention without provoking a severe immune response.

All references cited in this application are incorporated herein by reference. Having now generally described the invention, the following examples further describe the materials and methods used in carrying out the invention. The examples are not intended to limit the invention in any manner.

EXAMPLES

Materials.—Fibrinogen (Mosher and Blout, *J. Biol. Chem.* 248:6896 (1973)) and gelsolin (Chaponnier et al., *J. Cell. Biol.* 103:1473 (1986)) were purified from human blood plasma, and actin from rabbit skeletal muscle, by previously described methods (Janmey et al., *J. Biol. Chem.* 261:8357 (1986)). Actin was labeled with pyrene-iodoacetamide or tetramethylrhodamine 5-(and-6)-iodoacetimide (T-488, Molecular Probes, Eugene, Oreg.) as described elsewhere (Symons and Mitchison, *J. Cell. Biol.* 114:503 (1991)). Vitamin D-binding protein was either prepared from human blood by affinity chromatography using actin-Sepharose (Haddad et al., *Anal. Biochem.* 146:96 (1985)) or purchased from Calbiochem (San Diego, Calif.). Both materials showed similar affinity for actin based on their ability to inhibit actin polymerization as measured by changes in pyrene-labeled actin fluorescence. Thrombin from human plasma Cr-6759, Sigma, St. Louis, Mo.) and plasmin (810655 Kabi Vitrum, Franklin, Ohio) were diluted to 100 unit/ml and 10 unit/ml, respectively, with water and frozen immediately. Aliquots were thawed, kept at 4° C. and used within 10 hours. Rhodamine-labeled phalloidin was obtained from Molecular Probes, fluorescein-labeled avidin from Enzo Diagnostics NY, and DNase I from Boehringer Mannheim (Indianapolis, Ind.).

Example I—Viscoelastic measurements

The viscoelastic properties of fibrin gels were determined by rheologic measurements using either a Rheometrics instrument or a torsion pendulum. The principle behind these measurements is that when a force is applied in a direction parallel to the face of a sample (a shear force, or stress=force/area given in units of Pa=10 dyne/era$^2$) a viscoelastic sample deforms to an extent (the strain, a unitless quantity) that depends on the magnitude of the stress, and on the length of time that the stress is applied. Part of the energy of deformation is stored elastically in the material and part is dissipated by the slow viscous motion of the sample leading to irrecoverable deformation after the stress is removed. These viscoelastic properties can be quantitatively described by the shear modulus: the ratio of stress to strain, which is itself a function of time, and for some materials and extents of deformation, also of the strain. Often, the storage and loss (viscous) shear moduli are measured by applying oscillating deformations, and then the shear moduli, termed G' for the storage and G" for the loss modulus, are calculated from the magnitude and phase shift between oscillating stresses and strains.

The Rheometrics device applies an oscillating shear deformation to a sample confined between a cone and a plate, and it enables measurements of the elastic storage modulus, G', as a function of time, frequency, or deformation amplitude. The torsion pendulum can either measure the dynamic shear modulus from free oscillation or the shear compliance (ratio of strain to stress) from measurements of the deformation (strain) when a constant shear stress is applied to a disk-shaped sample held between plates of the pendulum. The principles of operation of these two instruments are described elsewhere (Janmey et al., *Biochemistry* 27:8218 (1988); Janmey, P., *J. Biochem. Biophys. Meth.* 22:41 (1991)).

In both instruments, the fibrin or fibrin/actin gel is formed between the plates of the rheometer by placing 400 μl–800 μl of a protein solution on the bottom plate immediately after addition of thrombin to initiate fibrin polymerization. The thrombin concentration was chosen to give a clotting time of a few minutes, which permitted time to position the sample in the rheometer before clotting occurred. Measurements were typically started one minute after the sample was placed between the plates and the clotting time was approximately 3 minutes. Measurements of strain dependence were made on samples aged for 90 minutes, or at least 30 times the clotting time, to ensure that clot formation was nearly complete and unchanged during the course of these measurements. When actin or actin/gelsolin complexes were added to the fibrinogen solution, G-actin was first polymerized to F-actin in the presence or absence of gelsolin by incubation for 1 hour in buffers containing 2 mM MgCl$_2$ and 150 mM KCl.

Viscoelastic properties of fibrin-actin gels. The presence of actin filaments during the polymerization of fibrinogen strongly affects the mechanical properties of the fibrin gel network. FIG. 1 shows the effect on the shear modulus, a measure of the clot's elastic resistance to deforming stresses, when increasing amounts of F-actin are incorporated into the clot. F-actin increases the shear modulus to an extent that depends on the actin concentration. The viscoelasticity of the actin filaments themselves may account for some of the increased shear modulus, but a significant component also results from the alteration of fibrin gel structure caused by inhibition of protofilament bundling previously described (Janmey et al., *Biochim. Biophys. Acta* 841:151 (1985)). The effect of F-actin is to make the clot finer, and finer clots might be expected to have lower shear moduli than coarse clots since they contain thinner filaments. However, fine clots may also exhibit higher shear moduli if the inhibition of fibrin bundle formation is coupled to an increase in the number of branch points (Roberts et al., *Biorheology* 10:29 (1973); Rosser et al., *Biophys. Chem.* 7:153 (1977)), and higher shear moduli for finer clots have been reported for fibrin polymerized in the presence of IgG (Gabriel et al., *J. Lab. Clin. Med.* 101:545 (1983)).

Figure 2:
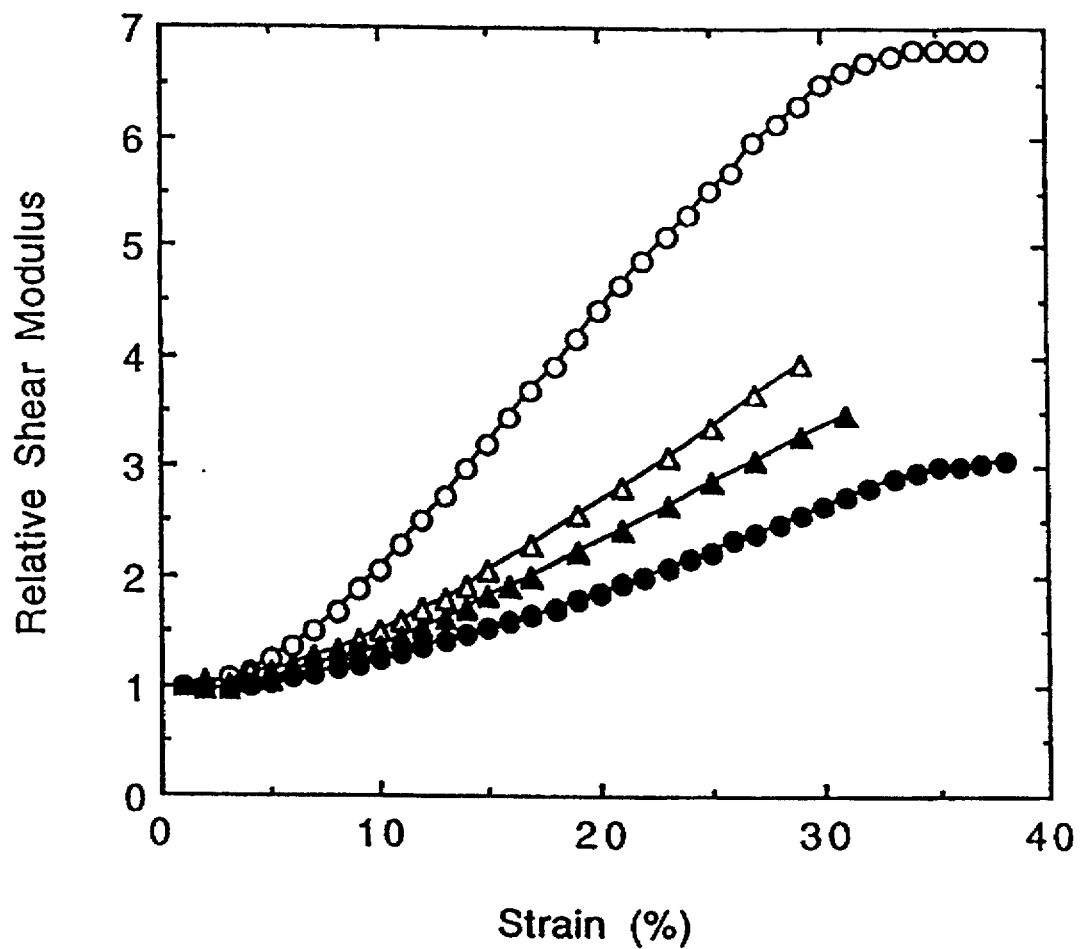
FIG. 2. Elimination of strain hardening by F-actin in fibrin gels. The shear modulus of fibrin gels containing various concentrations of F-actin at the concentrations shown measured over a range of strains at a constant angular frequency of 10 rad/s (1.6 Hz). Reaction conditions and meanings of symbols are given in the legend to FIG. 1.

One of the striking viscoelastic properties of fibrin gels is that they are strain-hardening: their elastic modulus increases with increasing amplitudes of deformation. FIG. 2 shows that this feature of fibrin rheology, which may be crucial for its physiologic function as a pliable, but rupture-resistant hemostatic plug, is nearly completely eliminated by long F-actin filaments.

Figure 3A:
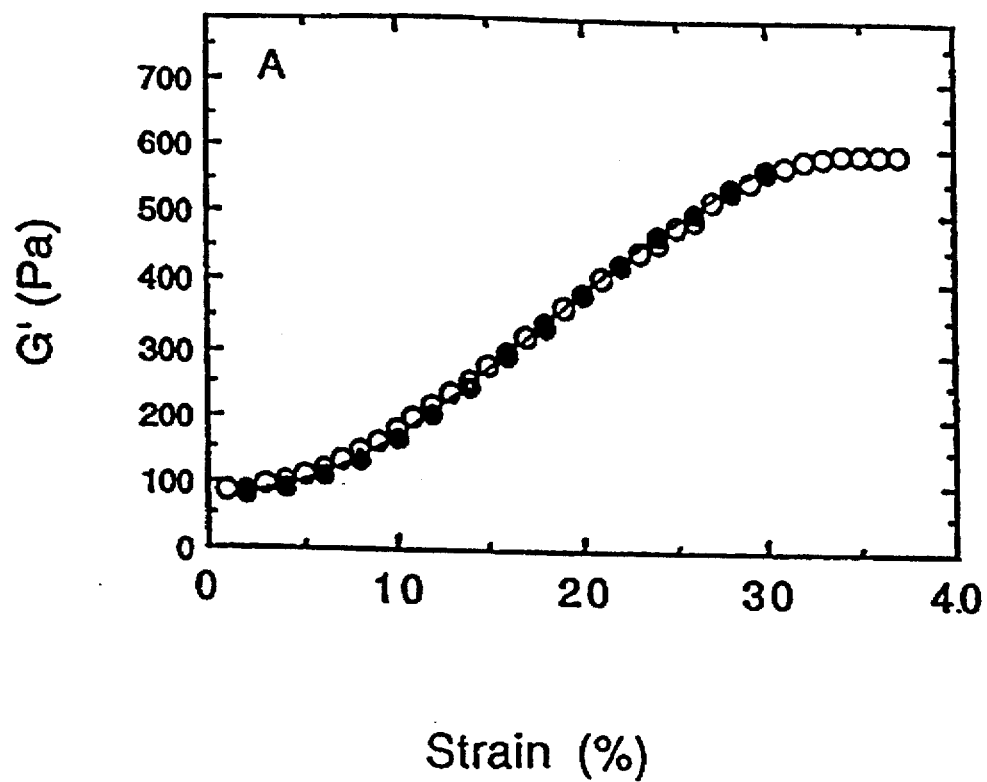
FIG. 3. Shortening of F-actin by gelsolin reverses its effect on strain hardening and hysteresis of fibrin. The shear modulus G' is shown for measurements at 10 rad/s over a range of strain amplitudes beginning at 1% and increasing to 37% (FIG. 3A) or 30% (FIGS. 3B and 3C) (open circles). Following deformation at the maximal strain amplitude, measurements of G' were repeated at sequentially decreasing maximal strain amplitudes to ascertain the recovery of samples after deformation (closed circles). The three Figures show results for 2 mg/ml fibrin alone (FIG. 3A); fibrin plus 0.2 mg/ml F-actin (FIG. 3B); and fibrin plus actin oligomers (3:1 actin:gelsolin complexes) (FIG. 3C). Other conditions are given in the legend to FIG. 1.
Figure 3B:
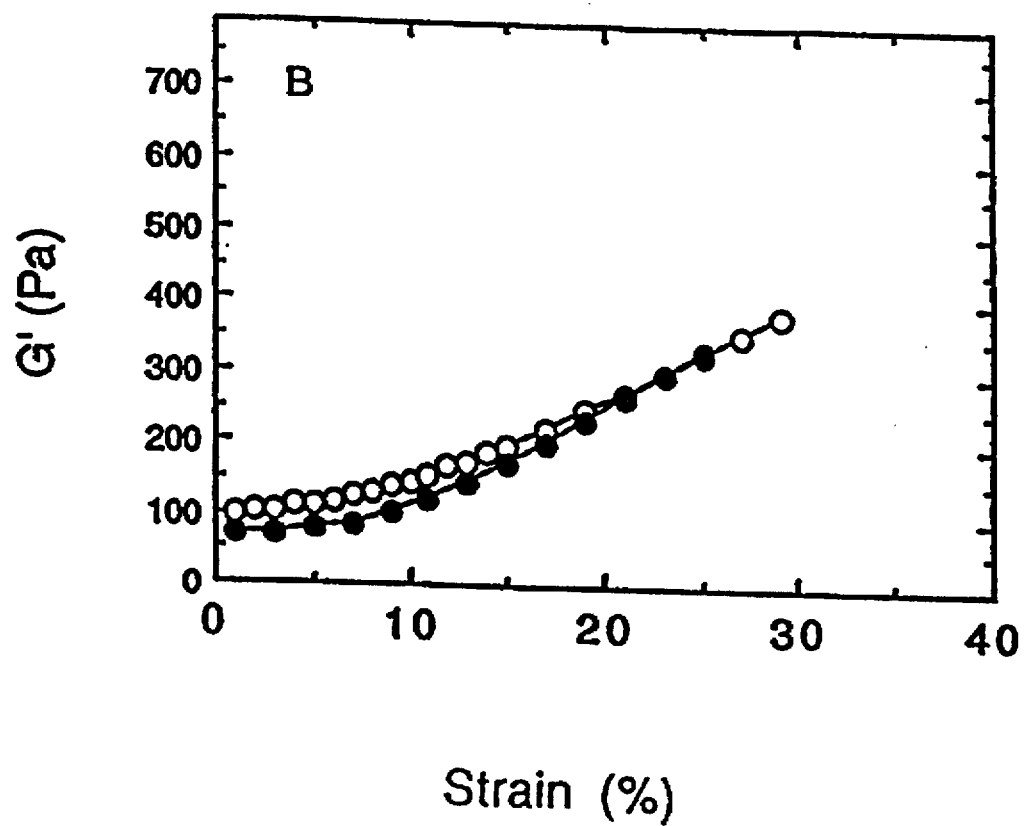
Figure 3C:
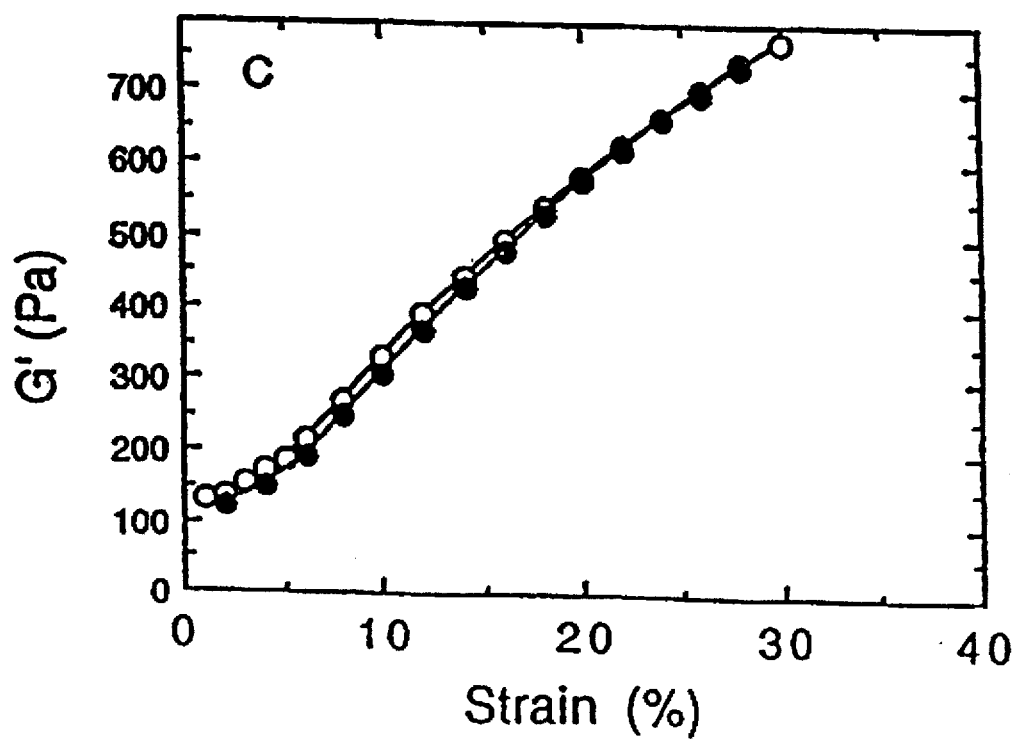

Not only does actin inhibit the strain-hardening of fibrin, it also reduces the elastic recovery of the clots. FIG. 3A shows the nearly total reversibility in the shear modulus observed when a fibrin gel is first deformed in increments to large maximal strain and then strained to successively smaller deformations. The reproducibility of G' after these large deformations reflects the high degree of elasticity Of these gels and their resistance to mechanical failure even when highly deformed. The presence of even a low amount (0.2 mg/ml) of F-actin reduces the degree of strain-hardening and leads to irreversible decreases of approximately 40% in the shear modulus after straining, indicating that fibrin/actin gels are damaged by deformations in the range that could occur in vivo (FIG. 3B). This phenomenon requires long actin filaments, because when the actin filaments are shortened by gelsolin, strain hardening is again observed, and the elastic recovery increases to levels near those of fibrin alone (FIG. 3C).

Example II—Binding Experiments

The amount of actin bound to fibrin was measured by the loss of solution fluorescence after incorporation of rhodamine-labeled actin into 2 mg/ml fibrin clots. Clots were formed in borosilicate glass tissue culture tubes by the addition of 1.7 NIH unit/ml thrombin to 2 mg/ml fibrinogen in T7 (100 mM NaCl, 50 mM Tris-Cl, pH 7.4) with F-actin, polymerized in Buffer B (20 mM Tris, 0.5 mM ATP, 0.2 mM DTT, 0.2 mM CaCl$_2$, 150 mM KCl, 2 mM MgCl$_2$ pH 7.4). Fibrin gelation occurred within 10 minutes and the clots were incubated for 1–2 hr at 24° C. The insoluble clots, containing >97% of the total fibrin, were removed by winding onto a glass pipette, and the fluorescence of the remaining solution was determined. Prior to and following clot formation, fluorescence was determined with a Perkin Elmer LS-5B Luminescence Spectrometer with excitation at 547 nm and emission at 573 nm. Previous sedimentation assays of the rhodamine-labeled actin indicated that 15% of the total fluorescence was unbound or bound to non-functional actin and this value was subtracted from all readings. The percentage of total actin bound to the fibrin clot was calculated as % bound=$100(FL_o-FL_1)/FL_o$ where $FL_o$=initial fluorescence prior to fibrin polymerization and $FL_1$=fluorescence of solution minus fibrin clot.

Figure 4:
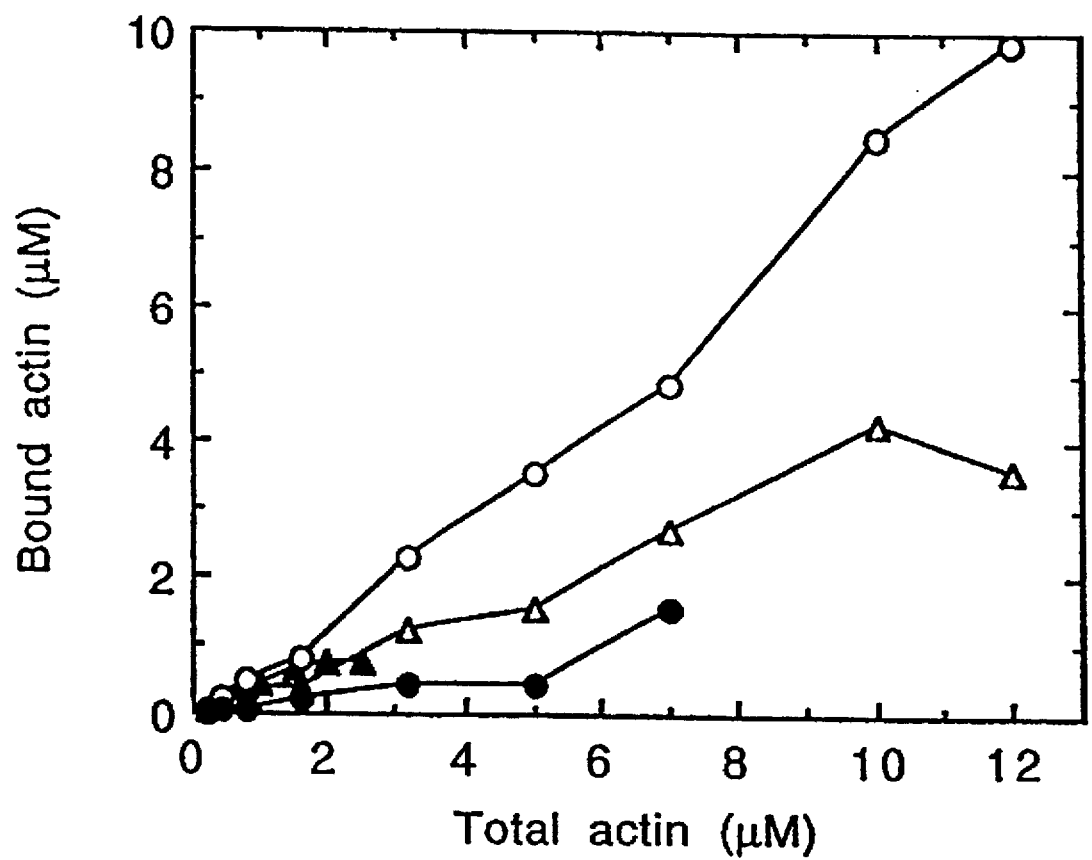
FIG. 4. Binding of actin filaments and complexes to fibrin gels. Various mounts of rhodamine-labeled F-actin alone (open circles) or actin polymerized in the presence of DBP (closed circles) or gelsolin (triangles) were added to fibrinogen (2 mg/ml; 6 µM) in T7 (100 mM NaCl; 50 mM Tris-Cl pH 7.4) prior to clot formation by addition of 1.7 NIH unit/ml thrombin. The molar ratio of DBP to actin was 2:1, and the molar ratio of gelsolin to actin was either 1:2 (closed triangles) or 1:12 (open triangles). The bound actin was removed from solution by winding the insoluble clot onto a glass pipette, and the amount of actin bound to the clot was measured from the difference between the fluorescence of the sample before and after clot removal, as described in the text.

Fibrin-actin binding. Binding assays showed that the amount of actin bound to fibrin clots depends on the length of the added actin filaments (FIG. 4). In the absence of actin-shortening proteins, binding appears to be unsaturable, and the molar ratio of actin to fibrin in the clot is greater than 1:1 at the highest actin concentrations shown. This finding is likely due to the fact that actin filaments polymerized in the absence of specific actin-binding proteins generally attain filament lengths of several microns (Pollard and Cooper, *Annu. Rev. Biochem.* 55:987 (1986)), and may not only bind to the fibrin clot but become entangled in it (Janmey et al., *Biochim. Biophys. Acta* 841:151 (1985)). When the filament length is limited by a 1:12 molar ratio of gelsolin (which results in gelsolin-capped filaments whose average length is 32 nm (Janmey et al., *J. Biol. Chem.* 261:8357 (1986)) binding appears to reach a limit at approximately a 2:3 molar ratio of actin to fibrin subunits (FIG. 4). If actin is prevented from polymerizing by incubation of G-actin monomers with the actin monomer-binding protein DBP (FIG. 4) the amount of actin bound to the clot is greatly decreased, but not entirely eliminated. Similar results were observed when actin was prevented from polymerizing by DNase I which forms tight complexes with actin monomers but binds actin at a different site than does DBP (data not shown). These results suggest that while long actin filaments may be trapped nonspecifically in the forming fibrin clot, specific binding of short filaments and complexed monomers also occurs. This binding is judged to be specific because both short (32 nm) actin filaments and complexes of actin monomers and DBP bind to clots whose average pore sizes are several microns in diameter (Rosser et al., *Biophys. Chem.* 7:153 (1977)). The affinity of actin monomers or filament fragments for the fibrin gel is difficult to evaluate precisely because the presence of actin perturbs the structure of the matrix to which it binds (Janmey et al., *Biochim. Biophys. Acta* 841:151 (1985)), but the data of FIG. 4 suggest that the affinity is sufficiently great ($Kd<1$ μM) that it would be significant at the concentrations of fibrin and actin likely to occur in vivo.

Figure 5:
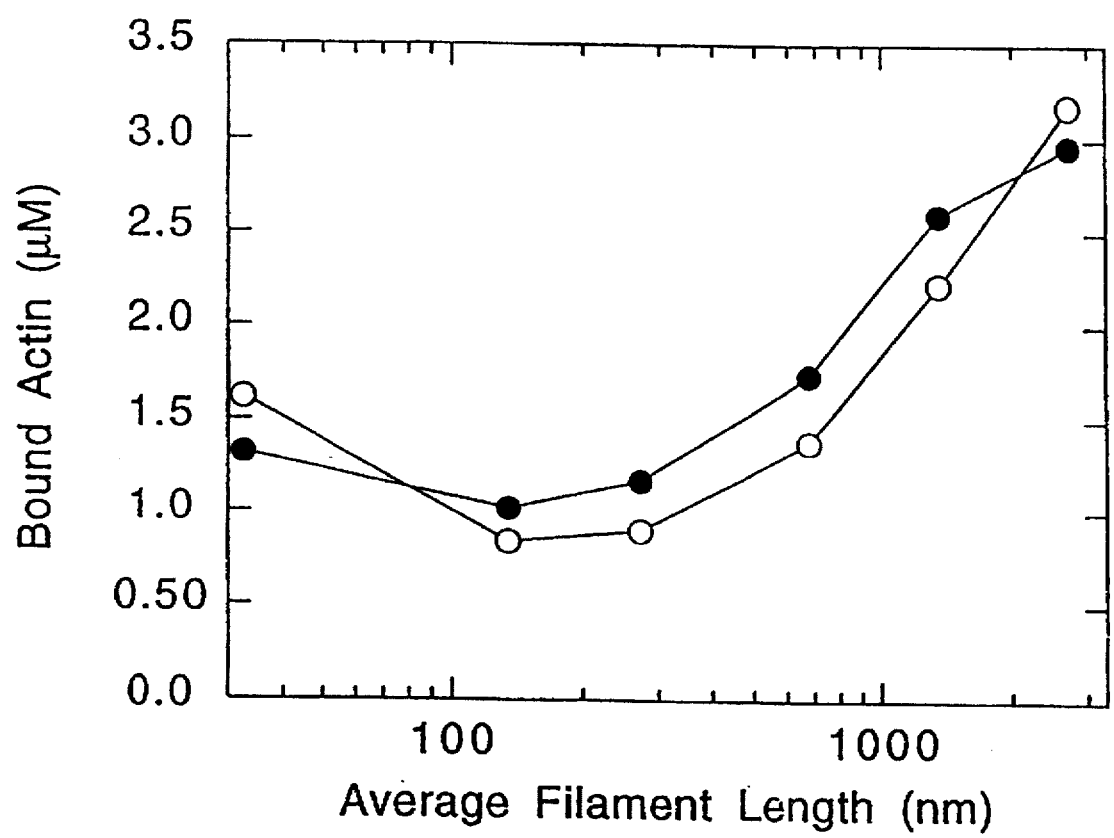
FIG. 5. Effect of $Ca^{2+}$ and actin filament length on the binding of actin to fibrin. Actin was polymerized with various molar ratios of gelsolin to produce filaments of average lengths ranging from 34 nm to 2.7 µm. 6 µM of the polymerized actin was mixed with 6 µM fibrinogen in solutions containing 100 mM NaCl and 50 mM Tris-Cl pH 7.4 either with (closed circles) or without (open circles) 3 mM $CaCl_2$, and the actin bound to fibrin following addition of 1.7 NIH unit/ml thrombin was measured as described in the text.

The effect of filament length on the amount of F-actin incorporated in the clot is shown in more detail in FIG. 5. In this experiment a constant amount of actin (12 μM; 0.5 mg/ml) was polymerized in the presence of various amounts of gelsolin and added to 6 μM fibrinogen (2.0 mg/ml) prior to addition of thrombin. Since each gelsolin nucleates and caps one filament, and under these solution conditions no uncapped filaments exist, the average number of actin subunits per filament equals the actin:gelsolin ratio (Janmey et al., *J. Biol. Chem.* 261:8357 (1986)), and the average length is calculated from the finding that there are 370 subunits in a micron of filament (Hanson and Lowy, *J. Mol. Biol.* 6:46 (1963)). By this calculation, the average length of actin filaments present in the solution of polymerizing fibrinogen ranged from 34 nm to 2.7 microns. More than 80 per cent of the total actin bound to the clot when the average filament length was very long, but even very short actin filaments, formed at high gelsolin:actin ratios bound significantly. Moreover, the binding of filaments shorter than 300 nm did not depend on their length, suggesting that the interaction is not due entirely to trapping of filament within the pores of the fibrin gel, but to a specific interaction between actin and fibrin. These results confirm that actin binds to fibrin in part independently of steric interactions. FIG. 5 also shows that the binding of F-actin to fibrin does not depend on changes in fibrin structure caused by millimolar calcium ion concentrations.

Example III—Confocal Microscopy 2 mg/ml fibrinogen was mixed with 6 μM rhodamine-actin in the presence or absence of gelsolin or DBP at molar ratios to actin of 1:4 or 2:1, respectively. Fibrin polymerization was initiated by the addition of 0.1 unit/ml thrombin and 10 μl of each solution was placed on a microscope slide in a humidified chamber consisting of a hydrated filter paper in a covered Petri dish. Approximately 5 minutes after addition of thrombin, at a time near the clotting time, a cover slip was applied to the sample and the edges sealed with nail polish. In a control experiment, 10 μM fluorescein-labeled avidin was mixed with fibrinogen and polymerization initiated by addition of thrombin. Beginning one minute after preparation of the slides, samples were examined using a Bio-Rad MRC 600 scanning laser confocal microscope attached to a Zeiss Axiovert microscope. A 100X (NA 1.3) Plan-neofluar objective was used for imaging, and the confocal aperture was set at the minimum opening. This helped to eliminate fluorescence above and below the plane of focus, thereby increasing resolution and enabling us to visualize individual fibrin strands. The same laser setting, gain, and frames accumulated were used for all samples. This allowed for more accurate comparison of fluorescence intensities.

Figure 6A:
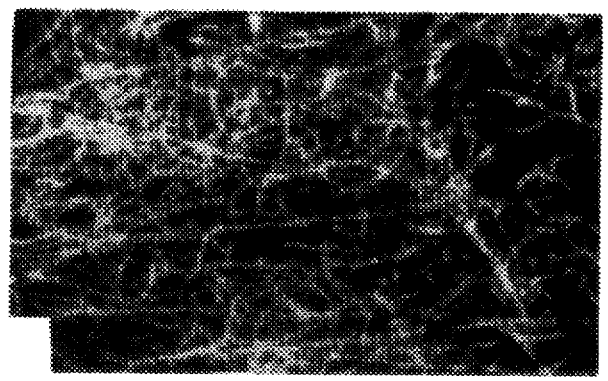
FIG. 6. Confocal fluorescence (FIGS. 6A, 6C, 6E, 6G and 6H) and phase contrast (FIGS. 6B, 6D and 6F) images of actin-containing fibrin clots. Addition of rhodamine-labeled F-actin to fibrinogen prior to thrombin-induced clot formation resulted in fluorescently labeled filaments (FIG. 6A). The corresponding phase contrast image (FIG. 6B) shows that the fluorescence of labeled actin co-localizes with the fibrin strands. Incubation of rhodamine-actin with gelsolin (FIGS. 6C and 6D) prior to clot formation resulted in reduced fluorescent labeling of the fibrin network. In the absence of thrombin the fluorescent actin filaments cannot be resolved with the confocal microscope (FIG. 6E). The corresponding phase contrast image (FIG. 6F) shows that a fibrin clot has not formed. Inhibition of actin polymerization by DBP resulted in reduced fluorescent labeling of fibrin strands (FIG. 6G). The specificity of the interaction of actin with fibrin is demonstrated in FIG. 6H which shows the absence of fluorescent fibrin when fluorescein-avidin was added to fibrinogen prior to thrombin-induced clot formation.
FIGS. 6C and 6G correlate with data showing reduced binding of actin monomers complexed with gelsolin and DBP to fibrin gels (see FIGS. 4 and 5). Bar in FIG 6H=9 µm for all Figures.
Figure 6B:
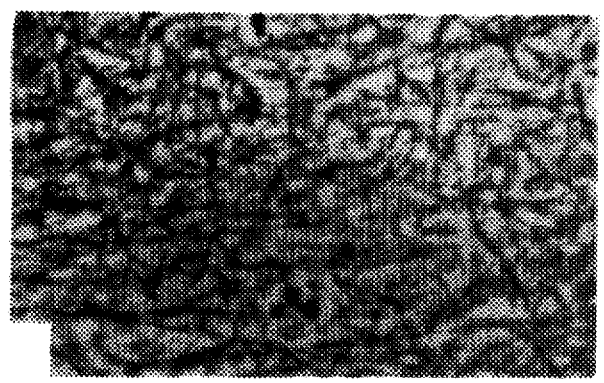
Figure 6C:
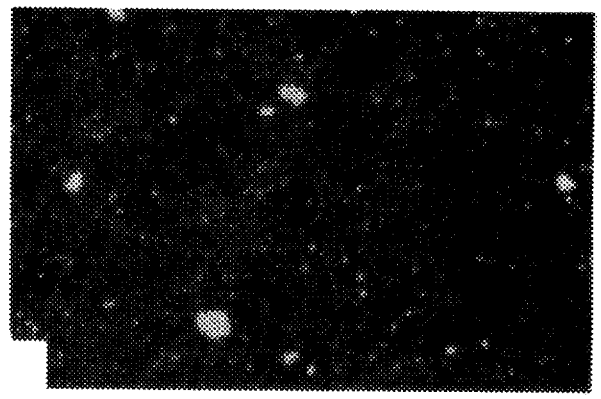
Figure 6D:
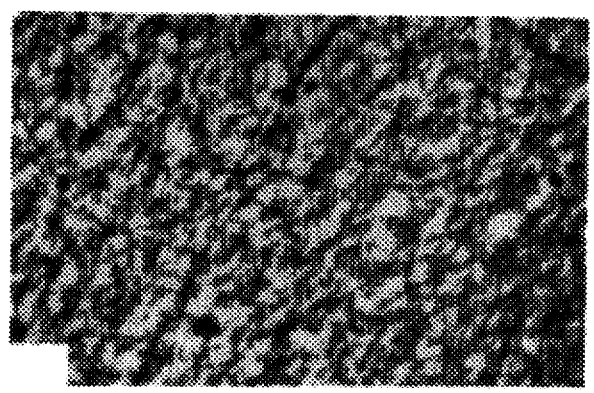
Figure 6E:
Figure 6F:
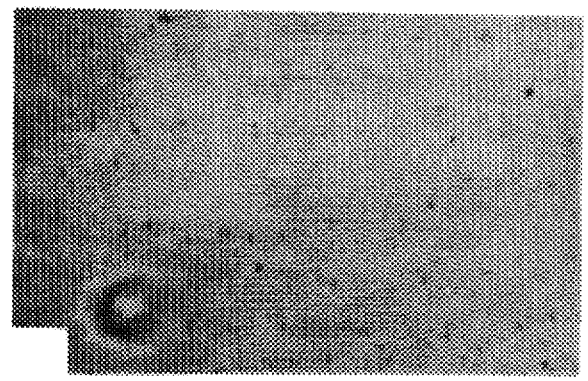
Figure 6G:
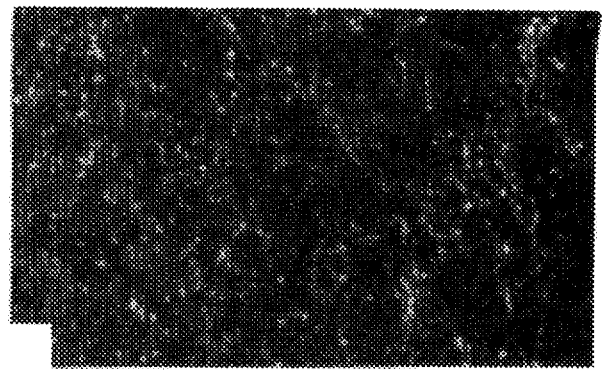
Figure 6H:
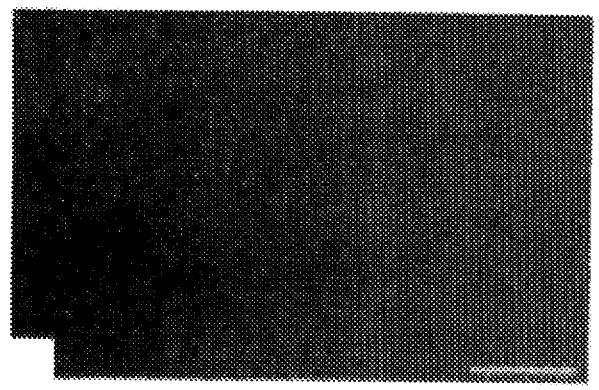

Fluorescence microscopy. Confocal microscopy of actin-containing fibrin clots was carried out to directly examine the interaction of actin with fibrin. FIG. 6a shows a typical fluorescence image obtained when rhodamine-labeled F-actin was added to a fibrinogen solution prior to clot formation, and FIG. 6b shows the corresponding phase contrast image of the fibrin strands. The fluorescence of the labeled F-actin coincides with the structure of the fibrin network, demonstrating the direct association of rhodamine-actin with fibrin. Similar images were obtained using fluorescein-labeled F-actin (data not shown). The coincidence of F-actin and fibrin strands suggests that these polymers associate laterally and do not interact entirely by a purely non-specific steric overlap. When the actin filament length is reduced to 32 nm by gelsolin, the fluorescent labeling of the fibrin network is much weaker (FIG. 6c) and some patches of bright fluorescence corresponding to spots of high density in phase contrast (FIG. 6d) are seen. These patches may represent sites at which short actin filaments bind or are trapped in the clot. The F-actin network in the absence of fibrin cannot be visualized by confocal microscopy since the thin (9 nm) actin filaments formed under these conditions do not form bundles (Janmey et al., *J. Biol. Chem.* 261:8357 (1986)) and therefore produce a network too fine to be resolved using confocal microscopy (FIGS. 6e and f). Incubation of rhodamine-actin with DBP before clot formation significantly reduced the intensity of the fluorescent labeling of fibrin, but a distinct pattern of fluorescence coincident with the fibrin strands was still visible (FIGS. 6g). These results are consistent with the data in FIGS. 4 and 5 which showed reduced, but still measurable binding of complexed actin monomers to fibrin clots. The specificity of the binding of F-actin to fibrin is supported by the finding that when fluorescein-avidin is added to a fibrinogen solution instead of rhodamine-labeled F-actin before clot formation, fluorescent labeling of the fibrin strands does not occur (FIG. 6h).

Example IV—Fibrinolysis Experiments

Actin-containing fibrin clots were lysed by two different methods. In the first, fibrin, with or without actin was polymerized by addition of a relatively high concentration of thrombin and a relatively low concentration of plasmin, chosen so that gelation was nearly complete before significant degradation of either fibrin or fibrinogen could occur, following the method of Shen et al. (Shen et al., *J. Biol. Chem.* 252:6184 (1977)). Fibrin gels were polymerized in a torsion pendulum and the rheologic properties of the clots measured during both clot formation and dissolution. The samples contained 3 g/l fibrin, 0.42 NIH units/ml thrombin and 0.3CU/ml plasmin in solutions containing 140 mM NaCl, 10 mM Tris-Cl, 2 mM $MgCl_2$, 2.5 mM $CaCl_2$, pH 7.4

In the second method, fibrin clots (6 μM) containing 6 μM filamentous rhodamine-actin were formed in borosilicate glass culture tubes by the addition of thrombin. Clotting was initiated by the addition of thrumbin (final concentration, 0.8 NIH units/ml). The clots were maintained at room temperature for 2 hours and then were gently removed from the tubes and soaked in an equal volume of buffer B (2 mM Tris, 0.5 mM ATP, 2 mM $CaCl_2$, 0.2 mM DTT, 150 mM KCl, 2 mM $MgCl_2$, pH 7.4) in the presence or absence of physiological quantities of gelsolin (2 μM). At various time intervals the solution surrounding the clot was removed and the fluorescence was measured to determine the amount of rhodamine label released from the clot.

Figure 7A:
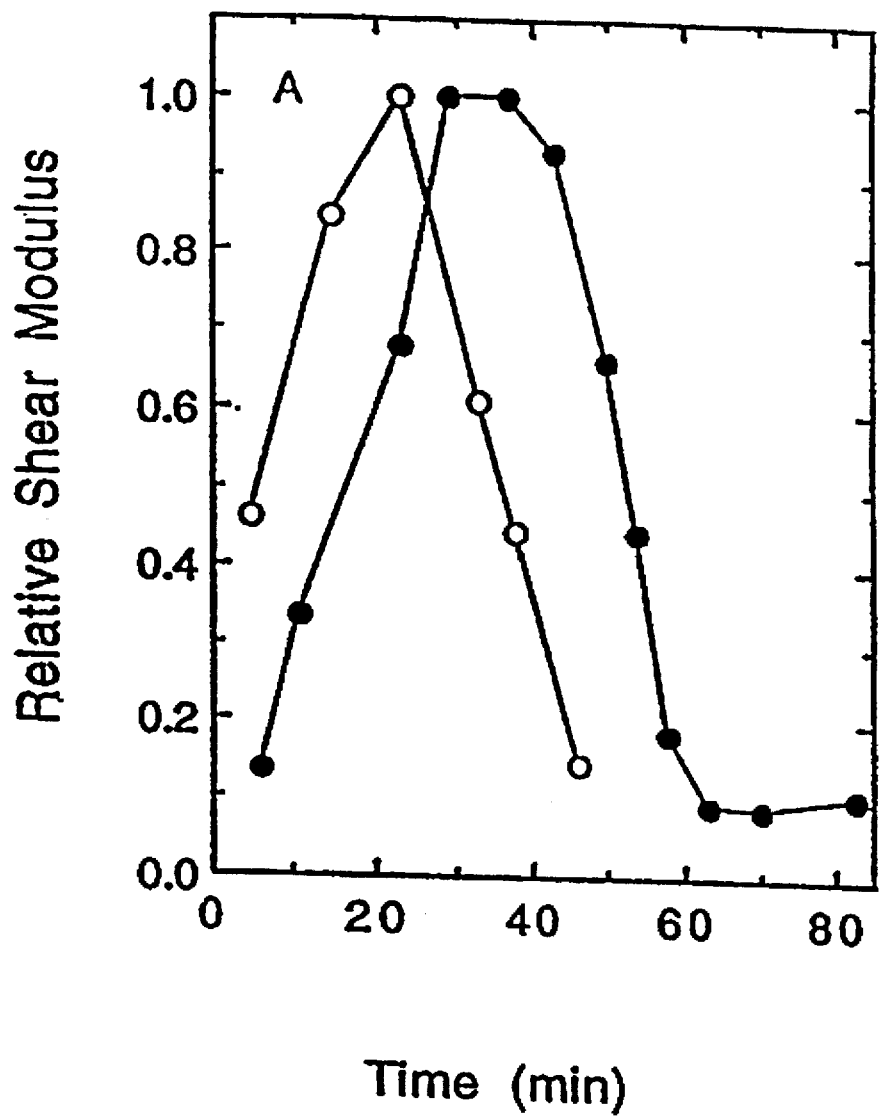
FIGS. 7A and 7B show results in the absence and presence of gelsolin at a 1:12 molar ratio to actin, respectively. All solutions contain 140 mM NaCl, 20 mM Tris-Cl, 2 mM $MgCl_2$, 2.5 mM $CaCl_2$, pH 7.4 with 0.4 NIH unit/ml thrombin and 0.3 units/ml plasmin.
Figure 7B:
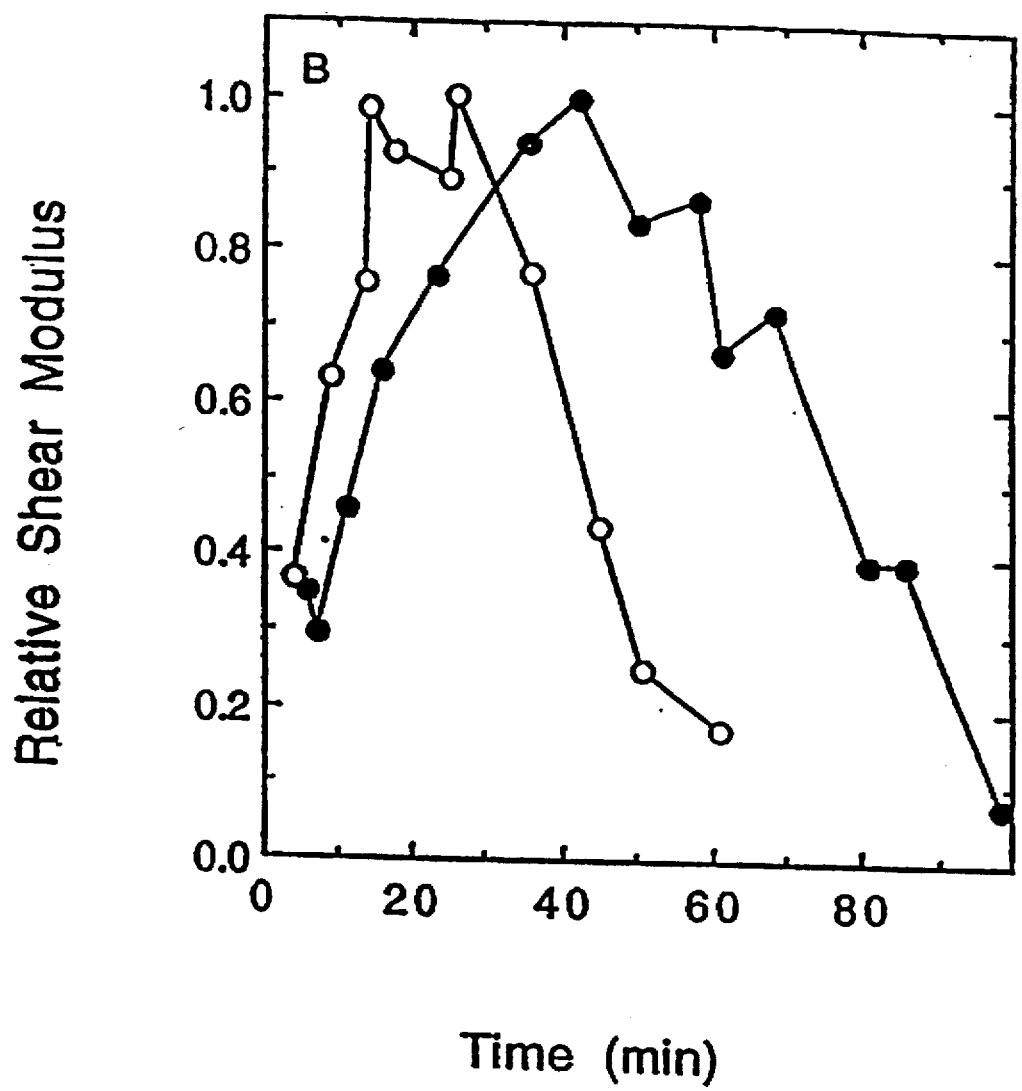

Effect of actin filaments on lysis of fibrin clots. Incorporation of actin into a fibrin clot results in inhibition of its rate of lysis by plasmin, as measured by release of radioactive fibrin fragments (Lind and Smith, *J. Biol. Chem.* 266:5273 (1991)), which is most obvious after several hours. Because the loss of a clot's structural integrity (as reflected in its elastic modulus) is one of the first consequences of lysis (Shen et al., *J. Biol. Chem.* 252:6184 (1977)), we performed the experiments shown in FIG. 7 to determine if actin's effect upon clot lysis could be detected at an earlier time. Incorporation of long (FIG. 7A) and short (FIG. 7B) actin filaments into fibrin gels retarded both the increase in shear modulus during clot formation and the plasmin-induced decrease in shear modulus during lysis. The effects of incorporated (both fibrin-bound and sterically trapped) actin filaments was evident 20 minutes after lysis began. Thus, the effects of actin incorporation into a clot results in a more rapid change in the physical properties of the clot under lyric conditions than is reflected by the rate of release of fibrin fragments into the lysis bath. Control viscoelastic measurements verified that F-actin itself was not degraded by plasmin during the time course of these experiments (data not shown).

Example V—Elution of Actin From Fibrin Clots

Because it is of potential therapeutic importance to know whether actin filaments trapped in fibrin clots may be eluted from the clot, actin-containing clots were incubated in the presence or absence of plasma gelsolin. Purified fibrinogen was prepared at a concentration between 2 and 3 mg/ml in an imidazole or tris buffer. The pH was 7.4. The ionic strength was no more than 150 millimolar and optimally 100 millimolar. Calcium was present at 0.3 mM. Actin was present at a concentration of 6–20 μM. ATP was present at 10 μM–10 mM. It was then possible to form a 1 millimeter clot in a 1 centimeter diameter chromatography column by plugging the column, filling it with 0.5 ml of fibrinogen solution and clotting the fibrinogen with about a tenth of an NIH unit per millimeter of thrombin. This way, once the clot formed, it was mechanically strong enough to withstand fluid permeation without collapsing and porous enough to allow fluid permeation to occur at a rate of about 0.2 ml per minute.

The fibrinogen clot formed in about 1 to 10 minutes. After ten times the clotting time, between 1 and 10 centimeters of pressure was applied to the chromatography tube. That is, the fluid used to permeate the clot was held approximately between 1 and 10 centimeters above the top of the clot. The level of the incubating buffer was then adjusted until the flow rate was about 0.2 milliliters per minute. The meniscus of the clot was monitored for collapse. The pressure was monitored by observing the meniscus of the clot. Buffer was allowed to permeate through the clot. The buffer was identical to that in which the fibrinogen was dissolved (the buffer in which the clot was formed). This buffer did not contain gelsolin. The buffer washed the clot free of nonspecifically held protein. Gelsolin was then added to the buffer and washed through the clot for about 1 to 5 minutes. The actin contained in the clot was severed by the gelsolin and eluted. The eluted fractions were assayed for actin by SDS polyacrylamide gel electrophoresis and immunoblotting with anti-actin antibody. In earlier experiments, fluorescently labeled actin was monitored spectrophotometrically. By this method, it has been possible to remove about 80% of the total actin held in the clot by permeablizing it with solutions that contain between 1 and 5 micromolar gelsolin.

Figure 8:
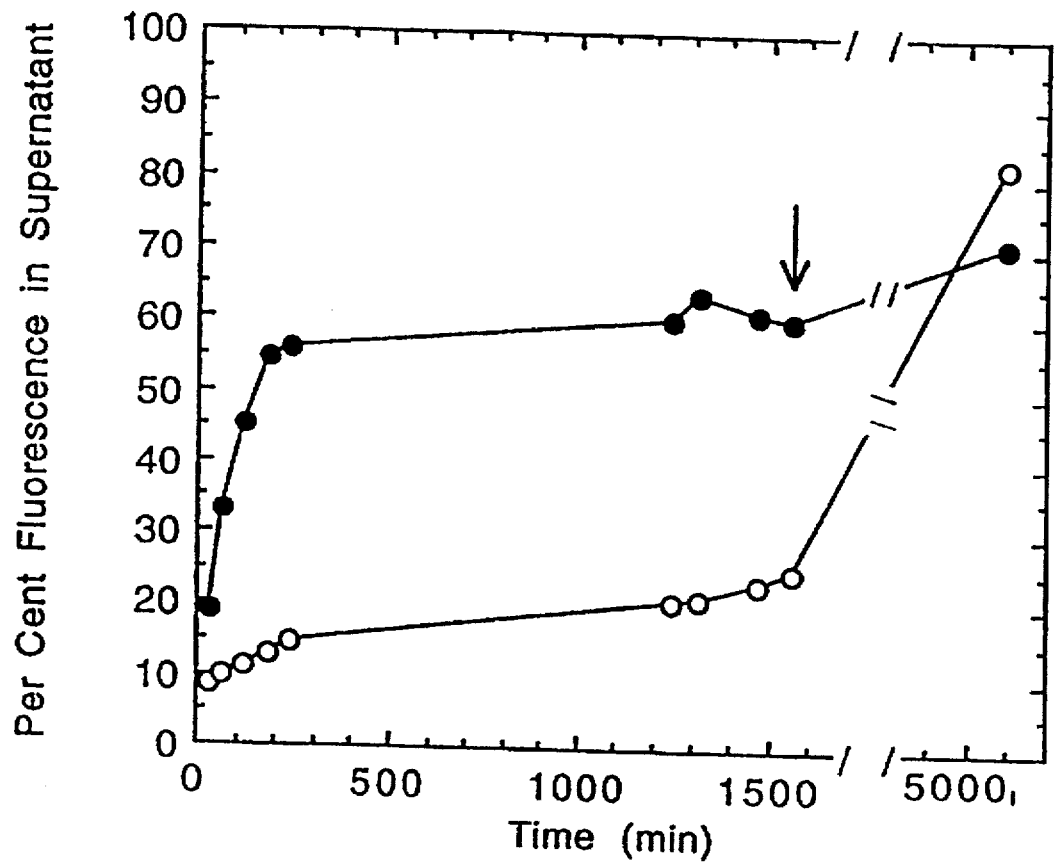
FIG. 8. Effect of external gelsolin on actin release from fibrin clot. Clots containing fibrin and actin were prepared in glass tubes by the addition of 1.5 NIH unit/ml thrombin. The concentrations of both the fibrinogen and rhodamine-labeled actin were 6 µM (2.0 mg/ml and 0.25 mg/ml, respectively). Once formed, clots were removed with glass pipettes and soaked in baths containing Buffer B (open circles) or Buffer B+0.2 mg/ml (2 µM) gelsolin (closed circles). Liberation of actin from the clot was measured as fluorescence released into the bathing medium, as described in the text. Maximal fluorescence release was obtained following clot lysis with 1.3 units/ml plasmin at the time indicated by the arrow.

As shown in FIG. 8, incubation of clots containing rhodamine-actin in physiologic (2 μM) concentrations of plasma gelsolin resulted in a loss of most of the actin from the clots. Since the fluorescence of rhodamine-labeled F-actin is higher than that of free rhodamine or rhodamine-actin monomers, the amount of label released into the medium may be somewhat underestimated by the fluorescence of the medium compared to that of the initial labeled F-actin solution. The amount of labeled actin that remains clot-associated is consistent with the results shown in FIG. 2. Further, elution of actin from the clots restored their susceptibility to plasmin-mediated lysis, as judged visually. Inspection after 18 hours revealed macroscopic remnants of those clots that had not been exposed to plasma gelsolin, while clots incubated in solutions containing plasma gelsolin were totally dissolved. The loss of clot-associated rhodamine does not reflect total clot lysis, but rather the known cleavage of the rhodamine-labeled terminal dipeptide of actin by plasmin (Mornet and Ue, *Proc. Natl. Acad. Sci. U.S.A.* 81:3680 (1984)).

Now having fully described this invention, it will be understood by those with skill in the art that the scope may be performed within a wide and equivalent range of condition, parameters, and the like, without affecting the spirit or scope of the invention or of any embodiment thereof.

What is claimed is:

1. A method for eluting and quantitating the actin in an actin-containing clot, comprising the steps of (1) removing plasma from a subject with tissue injury, (2) allowing said plasma to form a clot in vitro, (3) isolating said clot formed in step (2), (4) incubating said clot in liquid medium with at least one actin-binding protein, and (5) quantitating the amount of actin in said medium.

2. The method of claim 1, wherein said actin-binding protein is gelsolin or an active fragment thereof.

3. The method of claim 1, wherein said actin-binding protein is vitamin D binding protein or an active fragment thereof.

4. A method for reducing the amount of actin in an actin-containing clot in a subject comprising the step of infusing an efficacious level of at least one actin-binding protein into said subject with said actin-containing clot.

5. The method of claim 4, wherein said actin-binding protein is vitamin D binding protein or an active fragment thereof.

6. The method of claim 4, wherein said actin-binding protein is gelsolin or an active fragment thereof.

7. The method of claim 5, wherein said active fragment is the 45 kD, N-terminal chymotryptic fragment, CT45.

8. The method of claim 6, wherein said active fragment contains amino acid residues 25 through 165 of gelsolin.

9. The method of either of claims 2 or 6, wherein said active fragment contains amino acid residues 1 through 260 of gelsolin.

10. A method for restoring the normal viscoelastic properties and susceptibility to plasmin-mediated lysis to a fibrin clot formed in a subject after tissue injury, comprising the step of administering an efficacious level of at least one actin-binding protein to a subject with an actin-containing clot.

11. The method according to claim 10, wherein said actin-binding protein is vitamin D binding protein or an active fragment thereof.

12. The method according to claim 10, wherein said actin-binding protein is gelsolin or an active fragment thereof.

13. The method according to claim 12, wherein said active fragment is the 45 kD, N-terminal chymotryptic fragment, CT45.

14. The method according to claim 12, wherein said active fragment contains amino acid residues 25 through 165 of gelsolin.

15. The method according to claim 12, wherein said active fragment contains amino acid residues 1 through 260 of gelsolin.

16. The method according to any one of claims 1, 4 or 10, wherein two actin-binding proteins, gelsolin or a active fragment thereof and vitamin D binding protein or a active fragment thereof, are incubated with the clot, infused into the subject or administered to the subject, respectively.

* * * * *